United States Patent [19]

Temple, Jr. et al.

[11] Patent Number: 4,487,773

[45] Date of Patent: * Dec. 11, 1984

[54] 1,2,4-TRIAZOL-3-ONE ANTIDEPRESSANTS

[75] Inventors: Davis L. Temple, Jr.; Walter G. Lobeck, Jr., both of Evansville, Ind.

[73] Assignee: Mead Johnson & Company, Evansville, Ind.

[*] Notice: The portion of the term of this patent subsequent to Jul. 6, 1999 has been disclaimed.

[21] Appl. No.: 509,266

[22] Filed: Jun. 29, 1983

Related U.S. Application Data

[63] Continuation-in-part of Ser. No. 351,834, Feb. 24, 1982, abandoned, which is a continuation-in-part of Ser. No. 244,464, Mar. 16, 1981, Pat. No. 4,338,317.

[51] Int. Cl.$^3$ .................. C07D 249/08; C07D 403/04; A61K 31/495
[52] U.S. Cl. .................... 424/250; 544/295; 544/357; 544/360; 544/363; 544/366; 544/368; 546/276; 424/251
[58] Field of Search ............... 544/295, 357, 360, 366, 544/368, 363; 424/250, 251

[56] References Cited

U.S. PATENT DOCUMENTS 3,381,009  4/1968  Palazzo et al. ............... 544/366
3,857,845  12/1974 Palazzo ....................... 544/366
4,338,317  7/1982  Temple, Jr. et al. ........... 544/366
4,386,091  5/1983  Temple, Jr. et al. ........... 544/360

OTHER PUBLICATIONS

Silvestrini, et al., Int. J. Neuropharmacol., 7, 587–599, (1968).
Fabre, et al., Current Therapeutic Research, 25(6), 827–834, (1979).

*Primary Examiner*—Nicholas S. Rizzo
*Assistant Examiner*—S. A. Gibson
*Attorney, Agent, or Firm*—Robert H. Uloth; Richard P. Ryan

[57] ABSTRACT

Phenoxyalkyl substituted-1,2,4-triazolones having antidepressant properties typified by 2-[3-[4-(3-chlorophenyl)-1-piperazinyl]propyl]-5-ethyl-4-(2-phenoxyethyl)-2H-1,2,4-triazol-3(4H)-one are disclosed.

29 Claims, No Drawings

1,2,4-TRIAZOL-3-ONE ANTIDEPRESSANTS

CROSS-REFERENCE TO RELATED APPLICATION

This is a continuation-in-part application of Ser. No. 351,834 filed Feb. 24, 1982 and now abandoned which is a continuation-in-part of Ser. No. 244,464 filed Mar. 16, 1981 and now U.S. Pat. No. 4,338,317.

BACKGROUND OF THE INVENTION

The present invention relates to 1,2,4-triazole heterocyclic carbon compounds and to their preparation and use. More particularly, the invention relates to 2-[3-[4-(halophenyl)-1-piperazinyl]propyl]-5-ethyl-4-(phenoxyalkyl)-2H-1,2,4-triazol-3(4H)-ones and therapeutic use in treating depression.

U.S. Pat. No. 3,857,845 to G. Palazzo describes the compound 1-[3-(4-meta-chlorophenyl-1-piperazinyl)-propyl]-3,4-diethyl-$\Delta^2$-1,2,4-triazolin-5-one depicted structurally below.

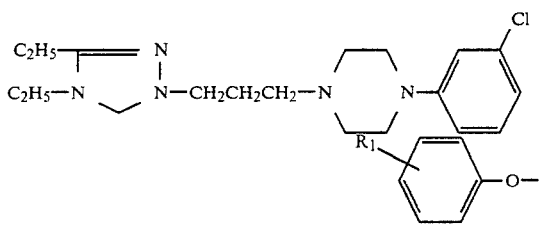

Alternatively, the compound can be named 2-[3-[4-(3-chlorophenyl)-1-piperazinyl]propyl]-4,5-diethyl-2H-1,2,4-triazol-3(4H)-one, and is commonly called etoperidone.

Regarding utility, the U.S. Pat. No. 3,857,845 Palazzo patent discloses that etoperidone has pharmacological properties typical of tranquilizers including sedation, reduced activity towards the experimentor and lower motor activity. In addition, hypotensive and analgesic activity are reported with possible use as an antianxiety agent and tranquilizer in human therapy mentioned.

U.S. Pat. No. 3,381,009 to G. Palazzo, et al., discloses 1,2,4-triazolo[4,3-a]pyridines of the following general formula

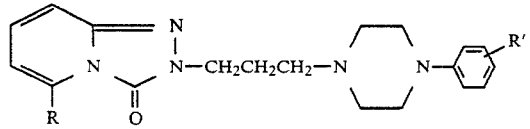

wherein R is hydrogen or methyl and R' is hydrogen, alkyl (1-4C), alkoxy (1-4C), or halogen. The compounds are said to exhibit tranqualizing action, hypotensive action, and analgesic action according to various animal tests. With respect to tranquilizing action, the pharmacological profile includes such behavioral effects as sedation, decrease in motor activity, hypotonia, high dose induced muscular non-coordination and ataxia, and inhibition of conditioned reflexes in the rat. According to the U.S. Pat. No. 3,381,009, data relative to behavioral, adrenolytic and anti-serotonin effects indicate that the compounds resemble major tranquilizers, such as chlorpromazine more than minor ones such as meprobamate. Pharmacological properties of one compound in particular, 2-[3-[4-(3-chlorophenyl)-1-piperazinyl]propyl]-1,2,4-triazolo[4,3-a]pyridin-3(2H)-one, have been described in more detail by Silvestrini, et al., International Journal of Neuropharmacology, 7, 587–599 (1968). The aforementioned compound, commonly known as trazodone, has been studied extensively in man and is considered to be an antidepressive equivalent in effectiveness to imipramine but with fewer side effects (Fabre, et al., Current Therapeutic Research, 25, 827–834 (1979)).

SUMMARY OF THE INVENTION AND DESCRIPTION OF PREFERRED EMBODIMENTS

Broadly described, the present invention is concerned with piperazinylalkyl-1,2,4-triazol-3-ones characterized by Formula I

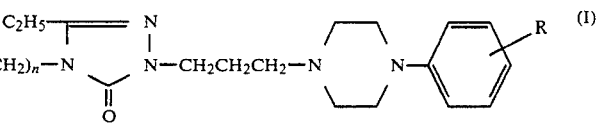

wherein n is the integer 2–4, R is halogen, $R_1$ is hydrogen, halogen or alkoxy, and pharmaceutically acceptable salts thereof. The term "halogen" or halo as used herein comprehends fluorine, iodine and most preferably bromine and chlorine. The term alkoxy as used herein comprehends from 1 to 4 carbon atoms, such as methoxy, ethoxy, tert-butoxy and the like.

Formula I comprehends compounds of U.S. patent application Ser. No. 244,464, particularly those wherein $R_1$ is hydrogen and n is 2. Thus, the new subject matter of the instant continuation-in-part application constitutes compounds of Formula I'

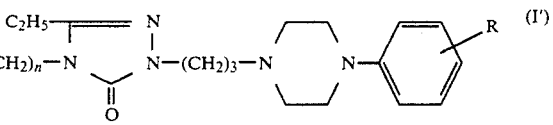

wherein R is halogen, $R_1$ is halogen or alkoxy when n is 2–4, $R_1$ is also hydrogen when n is 3–4, and pharmaceutically acceptable salts thereof.

The pharmaceutically acceptable acid addition salts are those in which the anion does not contribute significantly to the toxicity or pharmacological activity of the salt and, as such, they are the pharmacological equivalents of the bases of Formula I. They are generally preferred for medical usage. In some instances, they have physical properties which makes them more desirable for pharmaceutical formulation purposes such as solubility, lack of hygroscopicity, compressibility with respect to tablet formation and compatibility with other ingredients with which the substance may be used for pharmaceutical purposes. The salts are made by reaction of the base of Formula I with the selected acid preferably by contact in solution. They may also be made by metathesis or treatment with an ion exchange resin under conditions in which the anion of one salt of the substance of the Formula I is replaced by another anion under conditions which allow for separation of the desired species such as by precipitation from solution or extraction into a solvent, or elution from or retention on an ion exchange resin. Pharmaceutically acceptable acids for the purposes of salt formation of the substances of Formula I include hydrochloric, hydrobromic, hydroiodic, citric, acetic, benzoic, mandelic, phosphoric, nitric, mucic, isethionic, palmitic, heptanoic, and others.

In its most preferred embodiment, the present invention provides the compound of Formula I wherein R is meta-chloro which is 2-[3-[4-(3-chlorophenyl)-1-piperazinyl]propyl]-5-ethyl-4-(2-phenoxyethyl)-3H-1,2,4-triazol-3-one (Ia), alternatively named herein as 2-[3-[4-(3-chlorophenyl)-1-piperazinyl]propyl]-5-ethyl-2,4-dihydro-4(2-phenoxyethyl)-3H-1,2,4-triazol-3-one.

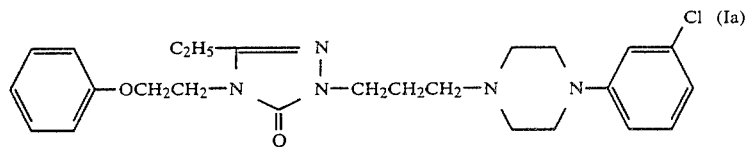

The Formula I compounds are useful pharmacological agents with psychotropic properties. In this regard, they exhibit selective central nervous system effects associated with antidepressant activity according to conventional in vivo test systems such as those listed below.

| Behavioral Test | Reference |
| --- | --- |
| Suppression of conditioned avoidance response (CAR) | Albert, et al., Pharmacologist, 4, 152 (1962). |
| Prevention of reserpine ptosis in mice (antidepressant) | Niemegeers, Industrial Pharmacology, Vol. 2 - Antidepressants. Ed. by S. Fielding and H. Lal, pp. 73-98, Futura, New York, N.Y., (1975). |
| Potentiation of alcohol Hypnois in the mouse (sedative) | — |

In these tests, 2-[3-[4-(3-chlorophenyl)-1-piperazinyl]-propyl]-5-ethyl-4-(2-phenoxyethyl)-2H-1,2,4-triazol-3(4H)-one (Ia) suppressed CAR in the rat and prevented but did not reverse reserpine ptosis in the mouse. Such activity is characteristic of most clinically useful antidepressant agents. Sedation is a common side effect of antidepressants. In this regard, compound Ia exhibited only minimal activity in potentiating alcohol hypnosis in the mouse which is indicative of a relative lack of this adverse reaction.

As further indication of the psychotropic activity and specificity of the instant compounds, state of the art in vitro central nervous system receptor binding methodology can be employed. Certain compounds (commonly referred to as ligands) have been identified which preferentially bind to specific high affinity sites in brain tissue dealing with psychotropic activity or potential for side effects. Inhibition of radiolabeled ligand binding to such specific high affinity sites is considered a measure of a compound's ability to affect corresponding central nervous system function or cause side effects in vivo.

The following tests, as well as others, can be employed in developing a profile of the psychotropic activity of the instant compounds.

| Receptor Binding Assay | Reference |
| --- | --- |
| Dopamine | Burt, et al., Molec. Pharmacol., 12, 800 (1976); Science, 196, 326 (1977); Creese, et al, Science, 192, 481 (1976). |
| Cholinergic | Yamamura, et al., Proc. Natn. Acad. Sci. USA 71 1725 (1974). |
| Alpha-receptor | Crews, et al., Science 202: 322 (1978). Rosenblatt, et al., Brain Res. 160: 186 (1979) U'Prichard, et al., Science 199: 197 (1978). U'Prichard, et al., Molec. Pharmacol. 13: 454 (1977). |
| Serotonin Type 2 | Peroutka and Snyder, Molec. Pharmacol. 16: 687 (1979). |

According to the foregoing assays, Compound Ia inhibits serotonin binding and was relatively inactive with respect to dopamine receptor binding, cholinergic receptor binding, and alpha-receptor binding. The latter is particularly significant in that drugs with high affinity for alpha-receptors relative to serotonin type 2 receptors are likely to cause side effects such as sedation and blood pressure lowering. Thus, the instant compounds and particularly Compound Ia are considered improved antidepressants with minimal side effect potential.

According to the present invention, the piperazinylalkyl-1,2,4-triazol-3-ones characterized by Formula I are obtained by the following process which comprises treating a piperazinylalkyltriazolone of Formula II

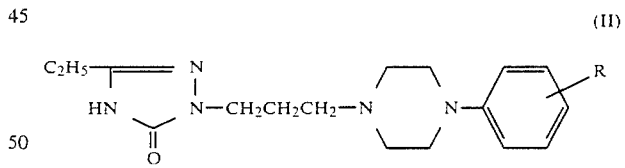

wherein R is halogen attached in the 2, 3 or 4 position of the phenyl ring with a suitable alkali metal base such as sodium hydroxide, potassium hydroxide, sodium carbonate or potassium carbonate to form an alkali metal salt thereof; and then alkylating the Formula II alkali metal salt with a phenoxyalkylhalide of Formula VII wherein R₁ is as defined above, n is the integer 2-4 and "X" comprehends halogen, preferably chlorine or bromine, or a suitable leaving group such as sulfate, phosphate, tosylate, mesylate, and the like

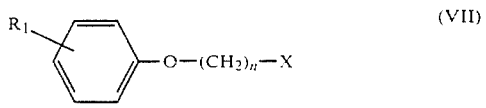

It is to be understood that Formula II depicts a tautomer of a compound with an alternate tautomeric form of Formula II'.

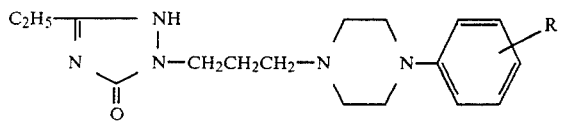
(II')

Standard labortory procedures are employed in carrying out the foregoing reaction such as those described for the alkylation step of the Gabriel synthesis—S. Gabriel, Ber. 20, 2224 (1887). In the present case, the reactants are combined in an inert reaction solvent at temperatures ranging from about 50° C. to 200° C. Acetonitrile and xylene are particularly preferred solvents for carrying out the reaction but other solvents which do not adversely affect the reaction or reactants can be employed. In this regard, solvents such as benzene, toluene dimethylformamide, n-butanol, and the like are suitable. The reaction period varies to some extent depending on solvent and temperature selected. For instance, at lower temperatures, long reaction periods are needed while at higher temperatures, alkylation is completed in a shorter time. In the case of acetonitrile or xylene, optimum yields are obtained with a reaction period of 8 to 68 hours.

A preferred process for preparing Formula I products comprises reacting a piperazinylalkyltriazolone of Formula II with a phenoxyalkylhalide of Formula VII in the presence of an alkali metal carbonate such as potassium carbonate or sodium carbonate in acetonitrile.

The Formula II piperazinylalkyltriazolone intermediates are preferably obtained by alkylating hydrazine with a 1-(halophenyl)-4-(3-halopropyl)piperazine to provide a 1-(halophenyl)-4-(3-hydrazinopropyl)piperazine of Formula III

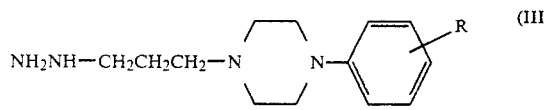
(III)

which is then condensed with N-ethoxycarbonylthiopropionamide

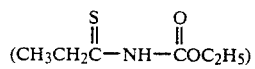

in a reaction inert solvent at elevated temperature. Alkanols, such as ethanol, are particularly preferred as solvents with the reaction conveniently carried out at reflux temperature. Other suitable solvents include acetone, acetonitrile, ethylacetate, dimethylformamide, ethers such as tetrahydrofuran and the like.

Another operable procedure for preparing Formula II intermediates comprises heating N-ethoxycarbonylthiopropionamide with hydrazine in ethanol to provide the triazolone compound of Formula IV

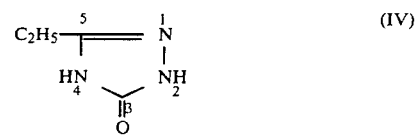
(IV)

which is then alkylated with a 1-(halophenyl)-4-(3-halopropyl)piperazine compound in xylene at reflux temperature. Compared to the previously described preparation of Formula II intermediates, this method is not as satisfactory in that the triazolone (IV) is alkylated indiscriminately at "two and four" positions resulting in lower yields of the desired piperazinylalkyltriazolone (II). For example, reaction of triazolone (IV) with 1-(3-phenyl)-4-(3-chloropropyl)piperazine in refluxing xylene affords the following compounds (isolated as hydrochloride salts) as secondary products in addition to the desired Formula (II) piperazinylalkyltriazolone intermediate wherein R is meta-chloro.

| Secondary Products |
|---|
| $A = -CH_2CH_2CH_2-N\underset{\diagdown\diagup}{\overset{\diagup\diagdown}{N}}-\bigcirc-Cl$ .HCl |
| 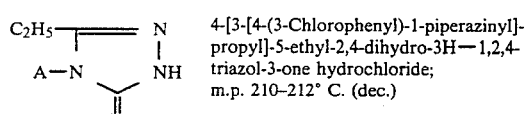 4-[3-[4-(3-Chlorophenyl)-1-piperazinyl]-propyl]-5-ethyl-2,4-dihydro-3H—1,2,4-triazol-3-one hydrochloride; m.p. 210–212° C. (dec.) |
| 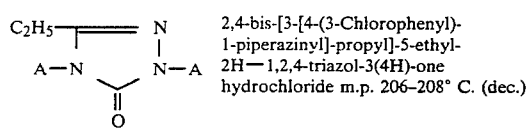 2,4-bis-[3-[4-(3-Chlorophenyl)-1-piperazinyl]-propyl]-5-ethyl-2H—1,2,4-triazol-3(4H)-one hydrochloride m.p. 206–208° C. (dec.) |

An alternate process for preparing a compound of Formula I comprises condensing a Formula III 1-(halophenyl)-4-(3-hydrazinopropyl)piperazine with a N-phenoxyethyl-N-ethoxycarbonylthiopropionamide of Formula (V) wherein $R_1$ is as defined above and n is 2-4.

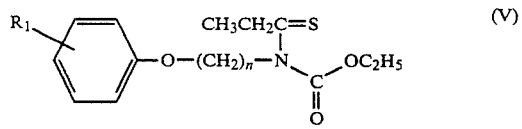
(V)

The condensation is carried out in a suitable reaction inert solvent such as ethanol as previously described for the preparation of the Formula (II) piperazinylalkyltriazolones. The Formula V intermediate can be obtained by standard methods such as condensing methyl dithiopropionate with a N-(phenoxyalkyl)ethylcarbonate under basic conditions or alkylating N-ethoxycarbonylthiopropionamide with a phenoxyalkylhalide of Formula VII in the presence of an alkali metal base.

The procedures hereinabove described for preparing Formula I compounds constitutes a unitary process which comprises condensing an amide of the Formula VI

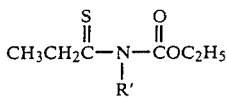 (VI)

wherein R' is hydrogen or $R_1$-phenoxyalkyl of 2 to 4 carbon atoms with a 1-(halophenyl)-4-(3-hydrazinopropyl)piperazine of Formula III

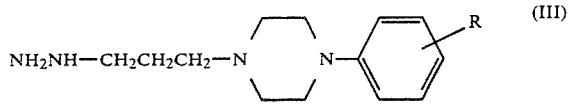 (III)

wherein R is halogen in a reaction inert solvent at elevated temperatures to provide compounds of Formula I when R' is $R_1$-phenoxyalkyl and compounds of Formula II when R' is hydrogen and thereafter alkylating a Formula II compound with a phenoxyalkyl halide of Formula VII in the presence of an alkali metal base.

A still further preferred process for preparing a compound of Formula I comprises alkylating a Formula VIII phenoxyalkyltriazolone

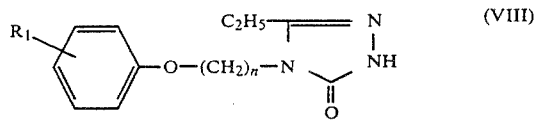 (VIII)

wherein $R_1$ is hydrogen, halogen or alkoxy, and n is the integer 2-4 with a 1-(halophenyl)-4-(3-halopropyl)piperazine of Formula IX

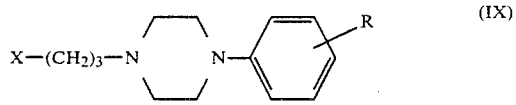 (IX)

wherein R is halogen and X comprehends halogen, preferably chlorine or bromine, or a suitable leaving group such as sulfate, phosphate, tosylate, mesylate, and the like, in the presence of a suitable alkali metal base such as sodium carbonate, potassium carbonate, potassium hydroxide and preferably sodium hydroxide in a reaction inert solvent. The term "reaction inert solvent" refers to any protic or aprotic solvent or diluent which does not enter into the reaction to any substantial degree. Laboratory procedures and solvents previously disclosed as operable for the alkylation of Formula II intermediates with Formula VII phenoxyalkyl halides are employed. In the instant case, alkanols, particularly isopropanol, are preferred.

The aforementioned preferred processes for preparing compounds of Formula I from triazolone intermediates of Formula II and VIII can be viewed as embodiments of a unitary process which comprises alkylating a compound of Formula X

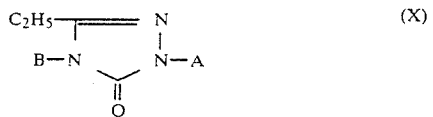 (X)

wherein A is hydrogen or a 1-(halophenyl)-4-(3-halopropyl)piperazine radical

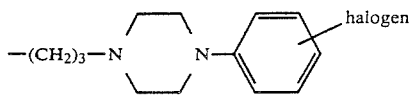

B is hydrogen or the phenoxyalkyl radical

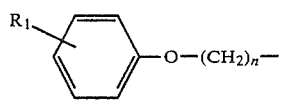

in which "$R_1$" is as defined above, "n" is the integer 2 to 4 and one of "A" or "B" must be hydrogen with an alkylating agent of Formula VII or IX.

Another aspect of the instant invention provides a method for treating a mammal afflicted with depression which comprises administering systemically to said mammal a therapeutically effective antidepressant amount of a compound of Formula I or Formula XI or a pharmaceutically acceptable acid addition salt thereof. An effective dose ranges from 0.01 to 40 mg/kg of body weight with the dosage dependent on effects sought, manner of administration, and to some extent with the particular compound selected. Systemic administration refers to oral, rectal and parenteral (i.e. intramuscular, intravenous and subcutaneous). Generally, it will be found that when a compound of the present invention is administered orally, a larger quantity of the active agent is required to produce the same effect as a smaller quantity given parenterally. In accordance with good clinical practice, it is preferred to administer the instant compounds at a concentration level that will produce effective antidepressant effects without causing any harmful or untoward side effects.

The compounds of the present invention may be administered for antidepressant purposes either as individual therapeutic agents or as mixtures with other therapeutic agents. Therapeutically, they are generally given as pharmaceutical compositions comprised of an antidepressant amount of a compound of Formula I or a pharmaceutically acceptable salt thereof and a pharmaceutically acceptable carrier. Pharmaceutical compositions which provide from about 1 to 500 mg. of the active ingredient per unit dose are preferred and are conventionally prepared as tablets, lozenges, capsules, powders, aqueous or oily suspensions, syrups, elixirs and aqueous solutions.

The nature of the pharmaceutical composition employed will, of course, depend on the desired route of administration. For example, oral compositions may be in the form of tablets or capsules and may contain conventional excipients such as binding agents (e.g. syrup, acacia, gelatin, sorbitol, tragacanth, or polyvinylpyrrolidone), fillers (e.g. lactose, sugar, maize-starch, calcium phosphate, sorbitol or glycine), lubricants (e.g. magnesium stearate, talc, polyethyleneglycol or silica), disintegrants (e.g. starch) and wetting agents (e.g. sodium lauryl sulfate). Solutions or suspensions of a Formula I compound with conventional pharmaceutical vehicles are employed for parenteral compositions such as an aqueous solution for intravenous injection or an oily suspension for intramuscular injection.

The following non-limiting examples illustrate the process and products of this invention. Nuclear magnetic responance (NMR) spectral characteristics refer to chemical shifts down field (δ) expressed as parts per million (ppm) versus tetramethylsilane as reference standard. The relative area reported for the various shifts corresponds to the number of hydrogen atoms in the individual substituent and the nature of the shifts as to multiplicity is reported as broad singlet (bs), multiplet (m), triplet (t), or qudruplet (q) with coupling constant reported where appropriate. The format is NMR (solvent): δ(relative area, multiplicity, J value). Abbreviations employed are DMSO-d$_6$ (deuterodimethylsulfoxide), IR (infrared), and KBr (potassium bromide).

EXAMPLE 1

2-[3-[4-(3-Chlorophenyl)-1-piperazinyl]propyl]-5-ethyl-1H-1,2,4-triazol-3(2H)-one* (IIa)

*Alternately named 2-[3-[4-(3-chlorophenyl)-1-piperazinyl]propyl]-5-ethyl-2,4-dihydro-3H-1,2,4-triazol-3-one.

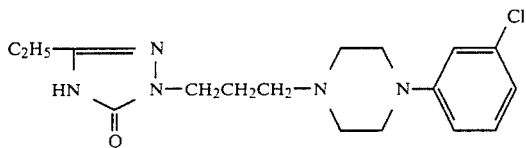

(a) 1-(3-Chloropropyl)-4-(3-chlorphenyl)piperazine Hydrochloride A 50% sodium hydroxide solution (430.6 g., 5.333 mole) is added dropwise to a stirred solution of 1-(3-chlorophenyl)piperazine hydrochloride (502.0 g., 2.153 mole) and 1-bromo-3-chloropropane (339.0 g., 2.153 mole) in 435 ml. water and 535 ml. acetone while maintaining temperature of 0°–10° C. Stirring is continued for a 16 hr. period at room temperature and the upper organic phase then separated and concentrated under reduced pressure. The remaining residual oil is taken up in 500 ml. acetone, filtered and the filtrate concentrated under reduced pressure to an oily residue which is dissolved in boiling dilute hydrochloric acid (1.67 liter water plus 280 ml. concentrated HCl, 3.36 mole). The oil which initially separates from the cooled acid solution, solidifies on standing and is collected, rinsed with cold water and air dried. Crystallization of this material from water employing activated charcoal affords 438.4 g. (66%) of 1-(3-chloropropyl)-4-(3-chlorophenyl)piperazine hydrochloride, m.p. 196.5°–198.5° C.

(b) 1-(3-Chlorphenyl)-4-(3-hydrazinopropyl)piperazine Hydrazine hydrate (10.7 g., 0.184 mole) in 20 ml. of ethanol is added slowly to 1-(3-chlorophenyl)-4-(3-chloropropyl)piperazine hydrochloride (9.29 g., 0.03 mole) in 20 ml. of ethanol. After refluxing the mixture for a 3 hr. period, the solvent is removed under reduced pressure and 20 ml. of water added to the residue. A 50 ml. portion of tetrahydrofuran is added to the aqueous mixture which is then saturated with potassium hydroxide pellets employing ice bath cooling. The tetrahydrofuran phase is separated, dried over magnesium sulfate and concentrated under reduced pressure to afford 7.4 g. (92%) of 1-(3-chlorophenyl)-4-(3-hydrazinopropyl)-piperazine employed without further purification in the following step.

(c) 2-[3-[4-(3-Chlorophenyl)-1-piperazinyl]propyl]-5-ethyl-1H-1,2,4-triazol-3(2H)-one. A solution of 1-(3-chlorophenyl)-4-(3-hydrazinopropyl)piperazine (19.6 g., 0.073 mole) in 90 ml. of ethanol is added to N-ethoxycarbonylthiopropionamide (12.13 g., 0.073 mole) in 30 ml. of ethanol. The mixture is refluxed for a 16 hr. period with evolution of hydrogen sulfide and then concentrated under reduced pressure. Crystallization of residual material from ethanol affords 18.3 g. (72%) of 2-[3-[4-(3-chlorophenyl)-1-piperazinyl]propyl]-5-ethyl-1H-1,2,4-triazol-3(2H)-one, m.p. 79°–81° C.

Addition of ethanolic hydrogen chloride to a sample of the base in ethanol with precipitation of the salt with ether affords 2-[3-[4-(3-chlorophenyl)-1-piperazinyl]-propyl]-5-ethyl-1H-1,2,4-triazol-3(2H)-one hydrochloride, m.p. 165°–167° C.

Anal. Calcd. for $C_{17}H_{24}ClN_5O \cdot HCl$: C, 52.86; H, 6.53; N, 18.13. Found: C, 52.72; H, 6.44; N, 17.96.

NMR (DMSO-d$_6$): 1.15 (3H,t, 7.3 Hz), 2.16 (2H,m), 2.43 (2H,q, 7.3 Hz), 3.18 (8H,m), 3.68 (4H,m), 6.89 (3H,m), 7.24 (1H,m), 11.49 (1H,bs).

IR (0.5% KBr, cm$^{-1}$): 770, 940, 1255, 1440, 1485, 1595, 1690, 2570, 2980.

EXAMPLE 2

2-[3-[4-(3-Chlorophenyl)-1-piperazinyl]propyl]-5-ethyl-4-(2-phenoxyethyl)-2H-1,2,4-triazol-3(4H)-one (Ia)*

*Alternately named 2-[3-[4-(3-chlorophenyl)-1-piperazinyl]propyl]-5-ethyl-2,4-dihydro-4-(2-phenoxyethyl)-3H-1,2,4-triazol-3-one.

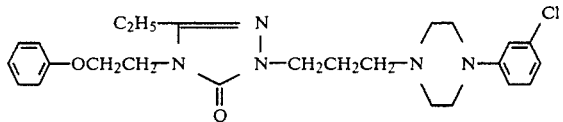

(a) Reaction in Xylene. Sodium hydroxide (2.08 g., 0.052 mole) in 10 ml. of water is added slowly to 2-[3-[4-(3-chlorophenyl)-1-piperazinyl]propyl]-5-ethyl-1H-1,2,4-triazol-3(2H)-one (18.2 g., 0.052 mole) in 150 ml. of warm ethanol with stirring. When mixing is complete, distillables are removed under reduced pressure. Ethanol is added to residual material and removed under reduced pressure and the process repeated until the sodium salt of 2-[3-[4-(3-chlorophenyl)-1-piperazinyl]propyl]-5-ethyl-1H-1,2,4-triazol-3(2H)-one is obtained as a hard solid.

The sodium salt is pulverized, suspended in 200 ml. of xylene and mixed with phenoxyethyl bromide (10.4 g., 0.052 mole) in 20 ml. of xylene. The resulting mixture is refluxed with stirring for a 64 hr. period and the hot reaction mixture filtered. The filtrate is concentrated under reduced pressure and residual material taken up in ether. Insolubles are collected and the ether filtrate concentrated to afford 22.9 g. (94%) of 2-[3-[4-(3-chlorophenyl)-1-piperazinyl]propyl]-5-ethyl-4-(2-phenoxyethyl)-2H-1,2,4-triazol-3(4H)-one as the free base. Purification of the product is carried out by acidifying a solution of the free base in ethanol with ethanolic hydrogen chloride, and crystallization to afford hydrated (0.25 mole) 2-[3-[4-(3-chlorophenyl)-1-piperazinyl]propyl]-5-ethyl-4-(2-phenoxyethyl)-2H-1,2,4-triazol-3(4H)-one hydrochloride, m.p. 175°–177° C. (30.7% yield).

Anal. Calcd. for $C_{25}H_{32}ClN_5O_2 \cdot HCl \cdot \frac{1}{4}H_2O$: C, 58.77; H, 6.61; N, 13.71. Found: C, 58.61; H, 6.48; N, 13.68.

NMR (DMSO-d$_6$): 1.20 (3H,t, 7.5 Hz), 2.16 (2H,m), 2.66 (2H,q, 7.5 Hz), 3.27 (8H,m), 3.74 (4H,m), 3.96 (2H,t), 4.17 (2H,t), 6.96 (6H,m), 7.29 (3H,m), 11.50 (1H,bs).

IR (0.5% KBr, cm$^{-1}$): 755, 940, 1235, 1440, 1490, 1595, 1710, 2580, 2940.

A sample of non-hydrated 2-[3-[4-(3-chlorophenyl)-1-piperazinyl]propyl]-5-ethyl-4-(2-phenoxyethyl)-2H-1,2,4-triazol-3(4H)-one hydrochloride obtained according to the above process melted at 175°–177° C.

Anal. Calcd. for $C_{25}H_{32}ClN_5O_2\cdot HCl$: C, 59.29; H, 6.57; N, 13.83. Found: C, 59.98; H, 6.44; N, 13.58.

NMR (DMSO-d$_6$): 1.20 (3H,t, 7.5 Hz), 2.14 (2H,m), 2.65 (2H,q, 7.5 Hz), 3.25 (8H,m), 3.72 (4H,m), 3.95 (2H,t), 4.16 (2H,t), 6.91 (6H,m), 7.25 (3H,m), 11.61 (1H,bs).

C$^{13}$NMR (DMSO-d$_6$): 9.65, 18.40, 22.90, 40.57, 41.89, 44.73, 50.31, 52.92, 64.95, 114.06, 114.30, 115.21, 119.12, 120.93, 129.53, 130.55, 133.94, 147.92, 150.78, 153.15, 157.87.

Ir (0.5% KBr, cm$^{-1}$): 750, 940, 1235, 1440, 1485, 1595, 1710, 2570, 2930.

(b) Reaction in Acetonitrile With Potassium Carbonate. A mixture of 2-[3-[4-(3-chlorophenyl)-1-piperazinyl]propyl]-5-ethyl-1H-1,2,4-triazol-3(2H)-one (15 g., 0.043 mole), phenoxyethyl bromide (8.62 g., 0.043 mole), potassium carbonate (11.9 g., 0.086 mole) and a trace of potassium iodide in 100 ml. of acetonitrile is refluxed for a 64 hr. period. The reaction mixture is filtered, the filtrate concentrated under reduced pressure and residual material taken up in ether and filtered. Concentration of the ethereal filtrate affords 18.35 g. (91%) of the free base product 2-[3-[4-(3-chlorophenyl)-1-piperazinyl]propyl]-5-ethyl-4-(2-phenoxyethyl)-2H-1,2,4-triazol-3(4h)-one. The free base is converted to the hydrochloride in ethanol employing ethanolic hydrogenchloride and crystallized from ethanol to afford a 53% yield of analytically pure 2-[3-[4-(3-chlorophenyl)-1-piperazinyl]propyl]-5-ethyl-4-(2-phenoxyethyl-2H-1,2,4-triazol-3(4H)-one hydrochloride, m.p. 175°–177° C.

Anal. Calcd. for $C_{25}H_{32}ClN_5O_2\cdot HCl$: C, 59.29; H, 6.57; N, 13.83. Found: C, 59.42; H, 6.68; N, 13.52.

NMR (DMSO-d$_6$): 1.20 (3H,t, 7.5 Hz), 2.15 (2H,m), 2.65 (2H,q, 7.5 Hz), 3.25 (8H,m), 3.72 (4H,m), 3.95 (2H,t), 4.16 (2H,t), 6.93 (6H,m), 7.27 (3H,m), 11.61 (1H,bs).

IR (0.5% KBr, cm$^{-1}$): 755, 940, 1240, 1440, 1490, 1595, 1710, 2580, 2940.

EXAMPLE 3

2-[3-[4-(3-Chlorophenyl)-1-piperazinyl]propyl]-5-ethyl-2,4-dihydro-4-(3-phenoxypropyl)-3H-1,2,4-triazol-3-one (Ib)

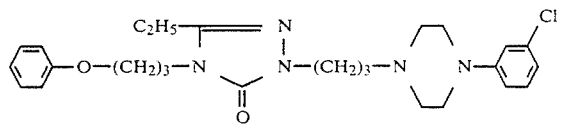

A mixture of 2-[3-[4-(3-chlorophenyl)-1-piperazinyl]propyl]-5-ethyl-1H-1,2,4-triazol-3(2H)-one (3.86 g., 0.01 mole), 3-phenoxypropyl bromide (2.15 g., 0.01 mole), potassium carbonate (4.15 g., 0.01 mole) and a trace of potassium iodide in 50 ml. of acetonitrile is refluxed for a 65 hr. period. The reaction mixture is filtered, the filtrate concentrated under reduced pressure and residual material taken up in ether and filtered. Solvent is removed and further purification carried out by sequentially converting the free base to the hydrochloride salt and then to the free base which is chromatographically treated employing a silica column with methanol/chloroform eluant. Free base, obtained from the chromatographic separation, is converted to the hydrochloride salt in ethanol employing ethanolic hydrogen chloride to afford 1.17 g., (22% yield) of analytically pure 2-[3-[4-(3-chlorophenyl)-1-piperazinyl]propyl]-5-ethyl-2,4-dihydro-4-(3-phenoxypropyl)-3H-1,2,4-triazol-3-one hydrochloride, m.p. 145°–147° C.

Anal. Calcd. for $C_{26}H_{34}ClN_5O_2\cdot HCl$: C, 60.00; H, 6.78; N, 13.46. Found: 60.27; H, 6.82; N, 13.67.

NMR (DMSO-d$_6$): 1.15 (3H,t, 7.2 Hz); 2.10 (4H,m); 2.55 (2H,q, 7.2 Hz); 3.18 (6H,m); 3.75 (8H,m); 3.99 (2H,t, 6.0 Hz); 6.94 (6H,m); 7.27 (3H,m); 11.70 (1H,bs).

EXAMPLE 4

2-[3-[4-(3-Chlorophenyl)-1-piperazinyl]propyl]-5-ethyl-2,4-dihydro-4-(4-phenoxybutyl)-3H-1,2,4-triazol-3-one (Ic)

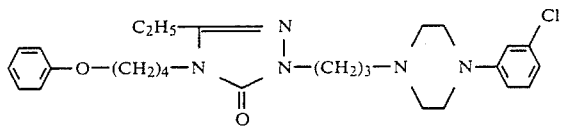

A mixture of 2-[3-[4-(3-chlorophenyl)-1-piperazinyl]propyl]-5-ethyl-1H-1,2,4-triazol-3-(2H)-one (3.86 g., 0.01 mole), 4-phenoxybutyl bromide (2.29 g., 0.01 mole), potassium carbonate (4.15 g., 0.01 mole) and a trace of potassium iodide in 50 ml. of acetonitrile is refluxed for a 65 hr. period. The reaction mixture is filtered, the filtrate concentrated under reduced pressure and residual material taken up in ether and filtered. Concentration of ethereal filtrate affords the free base. Conversion of the free base to the hydrochloride salt in ethanol with ethanolic hydrogen chloride and crystallization of the salt from ethanol affords analytically pure 2-[3-[4-(3-chlorophenyl)-1-piperazinyl]propyl]-5-ethyl-2,4-dihydro-4-(4-phenoxybutyl)-3H-1,2,4-triazol-3-one hydrochloride, m.p. 152°–154° C.

Anal. Calcd. for $C_{27}H_{36}ClN_5O_2\cdot HCl$: C, 60.68; H, 6.98; N, 13.11. Found: C, 60.70; H, 6.86; N, 13.25.

NMR (DMSO-d$_6$): 1.19 (3H, t, 7.4 Hz); 1.74 (4H.m); 2.19 (2H,m); 2.58 (2H,q, 7.4 Hz); 3.19 (6H,m); 3.70 (6H,m); 3.99 (4H,m); 6.92 (6H,m); 7.26 (3H,m); 11.70 (1H,bs).

EXAMPLE 5

5-Ethyl-4-(2-phenoxyethyl)-2H-1,2,4-triazol-3(4H)-one (VIIIa, n=2)

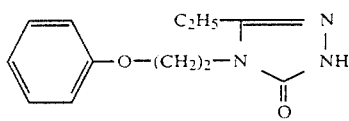

(a) 3-Phenoxypropionyl Hydrazide Hydrochloride. Ethyl 3-phenoxypropionate (1481.0 g., 7.62 mole) obtained according to R. Hall, et al., *J. Chem. Soc.*, 2035 (1949) is stirred in an ice bath during addition of 95% hydrazine (308.3 g., 9.14 mole). A precipitate forms and the mixture is allowed to stand at room temperature for 5 hr., then refrigerated for a 16 hr. period and filtered to provide 1128.0 g., of white solid (82.1% yield) of 3-phenoxypropionyl hydrazide. Preparation of the hydrochloride salt is carried out by dissolving 3-phenoxypropionyl hydrazide (2000.6 g., 11.1 mole) in 5 liters of methylene chloride. The solution is stirred and chilled in an ice bath as anhydrous hydrogen chloride is bubbled into the mixture to pH 3. Solid is collected, rinsed with methylene chloride and air dried to give 2100.0 g., (87.1% yield) of 3-phenoxypropionyl hydrazide hydrochloride, m.p. 145°–156° C.

(b) 1-Propionyl-4-(2-phenoxyethyl)semicarbazide. A mixture of 3-phenoxypropionyl hydrazide hydrochloride (938.9 g., 4.333 mole), 6.8 kg. ice-water and 3.4 liters toluene is stirred in an ice bath as a solution of sodium nitrate (328.6 g., 4.763 mole) in 1.4 liters of water is added over a 10 min. period. The mixture is stirred for 0.5 hrs. at 2° C., Celite added and the mixture filtered through a Celite bed. The filtrate layers are separated, and the aqueous layer extracted with two 400 ml. portions of toluene. Combined toluene extracts are dried over magnesium sulfate, filtered and the toluene solution of 3-phenoxypropionyl azide added over a 1.5 hr. period to a flask heated on a steam-bath under a nitrogen atmosphere with stirring. Following addition, decomposition of the azide to the phenoxyethyl isocyanate intermediate is completed by heating and stirring until gas evolution stops. The clear, yellow solution is cooled to 20° C. and propionyl hydrazide (381.8 g., 4.333 mole) obtained according to T. Rabini, et al., *J. Org. Chem.*, 30, 2486 (1965) is added in one portion with stirring. stirring is continued and the reaction mixture chilled to 10° C. and filtered affords 792.2 g., (72.8% yield) of 1-propionyl-4-(2-phenoxyethyl)semicarbazide, m.p. 178°–183° C.

(c) 5-Ethyl-4-(2-phenoxyethyl)-2H-1,2,4-triazol-3(4H)-one.

A solution of potassium hydroxide (88.4 g., 1.576 mole) in 10 liters of water is stirred and heated to 95° C.; then 1-propionyl-4-(2-phenoxyethyl)-semicarbazide (396.1 g., 1.576 mole) added and the mixture stirred at 95°–96° C. for a 40 min. period. Insolubles are collected and the filtrate stirred in an ice bath as 145 ml. (1.74 mole) of 37% hydrochloric acid is added. Stirring is continued with cooling to provide a white solid which is collected, rinsed with water and air dried to provide 233.5 g., (63.5% yield) of 5-ethyl-4-(2-phenoxyethyl)-2H-1,2,4-triazol-3(4H)-one, m.p. 136°–139° C.

Anal. Calcd. for $C_{12}H_{15}N_3O_2$: C, 61.79; H, 6.48; N, 18.01. Found: C, 61.77; H, 6.50; N, 17.91.

EXAMPLE 6

2-[3-[4-(3-Chlorophenyl)-1-piperazinyl]propyl]-5-ethyl-2,4-dihydro-4-(2-phenoxyethyl)-3H-1,2,4-triazol-3-one (Ia)

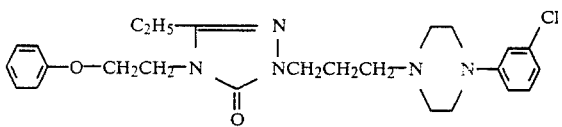

Reaction in Isopropanol with Sodium Hydroxide. A mixture of 5-ethyl-4-(2-phenoxyethyl)-2H-1,2,4-triazol-3(4H)-one (60.0 g., 0.257 mole), 1-(3-chlorophenyl)-4-(3-chloropropyl)piperazine hydrochloride (79.7 g., 0.257 mole), sodium hydroxide (26.7 g., 0.669 mole) and 400 ml. of isopropanol is stirred and heated at reflux for a period of 10 to 18 hrs. The mixture is acidified with 35 ml. (0.42 mole) of 37% hydrochloric acid and the solvent concentrated under reduced pressure. Residual material is stirred with 400 ml. of methylene chloride, filtered, and the filtrate concentrated under reduced pressure. Crystallization of the residue from 600 ml. of isopropanol affords 81.5 g. (62.5% yield) of product which is further crystallized from water and then isopropanol to provide 2-[3-[4-(3-chlorophenyl)-1-piperazinyl]propyl]-5-ethyl-2,4-dihydro-4-(2-phenoxyethyl)-3H-1,2,4-triazol-3-one hydrochloride, m.p. 180°–182.5° C.

Spectral (NMR, $^{13}C$ NMR, IR) and elemental analysis data are consistent and in accord with that obtained for the identical product of Example 2.

EXAMPLE 7

Additional Formula I Products

By substituting the enumerated phenoxyalkyl halide for phenoxyethyl bromide in Example 2, alkylation of 2-[3-[4-(3-chlorophenyl)-1-piperazinyl]propyl]-5-ethyl-1H-1,2,4-triazol-3(2H)-one is carried out to provide the indicated Formula I compounds.

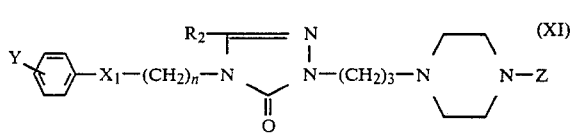

| Compound | | |
|---|---|---|
| $R_1$ | n | Phenoxyalkyl halide |
| (Id) 4-Cl | 2 | 4-chlorophenoxyethyl chloride |
| (Ie) 3-Cl | 2 | 3-chlorophenoxyethyl chloride |
| (If) 4-F | 2 | 4-fluorophenoxyethyl bromide |
| (Ig) 4-F | 3 | 4-fluorophenoxypropyl chloride |
| (Ih) 3-$CH_3O$ | 2 | 3-methoxyphenoxyethyl chloride |
| (Ii) 4-$CH_3O$ | 2 | 4-methoxyphenoxyethyl chloride |

FURTHER DETAILED DESCRIPTION OF THE INVENTION

A number of additional compounds similar to those defined by Formula (I) above have antidepressant properties. For instance, they inhibit serotonin type 2 binding at concentrations less than 1000 nanomolar, a characteristic of clinically useful antidepressants. Formula (XI) below redefines the scope of the invention to include all of these additional substances illustrated in Examples 8 and 9 and the subject matter of Formula (I'). Formula (XI) excludes the claimed subject matter of applicants' first filed U.S. patent application Ser. No. 244,464 which issued as U.S. Pat. No. 4,338,317 July 6, 1982. Thus the present invention comprehends a compound of Formula XI $$Y\text{—}\underset{}{\bigcirc}\text{—}X_1\text{—}(CH_2)_n\text{—}N\underset{\underset{O}{\|}}{\overset{R_2\text{—}\!=\!\text{—}N}{\diagup\!\!\diagdown}}N\text{—}(CH_2)_3\text{—}N\underset{}{\diagup\!\!\!\diagdown}N\text{—}Z \quad (XI)$$

wherein n is 2–4; $R_2$ is hydrogen or lower alkyl of 1 to 4 carbon; $X_1$ is oxygen or a direct bond; Y is hydrogen, halogen, lower alkoxy of 1 to 4 carbon or $CF_3$ with the proviso that when Y is hydrogen, n cannot be 2, $R_2$ cannot be ethyl, $X_1$ cannot be oxygen and Z cannot be phenyl having a mono halogen substituent; Z is benzyl or a radical selected from the group

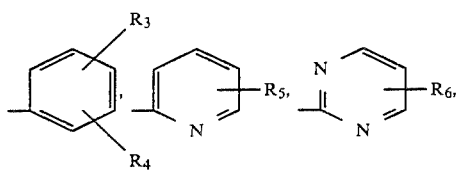

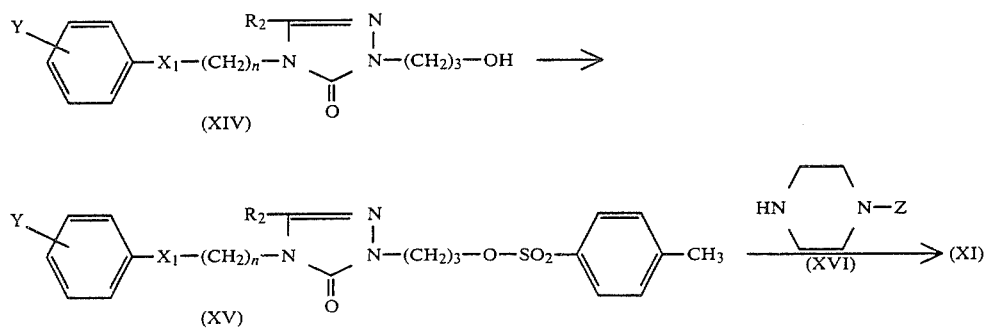

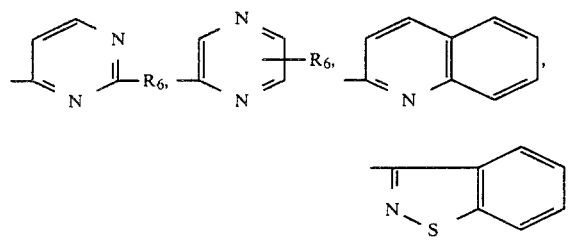

wherein $R_3$ is hydrogen or halogen; $R_4$ is halogen or $CF_3$; $R_5$ is hydrogen, halogen or cyano; $R_6$ is hydrogen or halogen; or a pharmaceutically acceptable acid addition salt thereof.

The compounds of Formula (XI) are obtained according to methods previously set forth or by modifications illustrated in the following scheme 1 and 2 flow diagrams.

Scheme 1

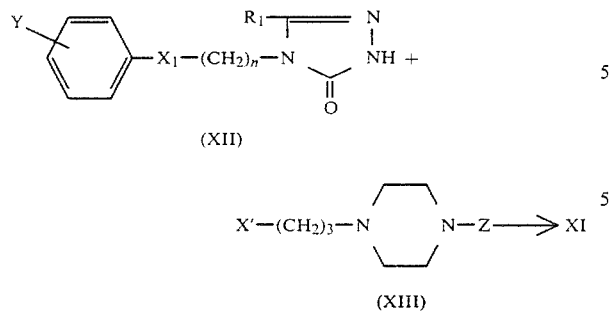

The process of Scheme 1 for preparing a compound of Formula (XI) comprises alkylating a Formula (XII) triazolone with a piperazinylpropyl-X' of Formula (XIII) wherein X' comprehends halogen (preferably chlorine or bromine) or a suitable leaving group such as sulfate, phosphate, tosylate, mesylate, and the like, in the presence of a suitable alkali metal base such as sodium carbonate, potassium carbonate, potassium hydroxide, sodium hydroxide or tetrabutylammonium hydrogen sulfate in a reaction inert solvent. A trace of potassium iodide is generally used as a catalyst. Laboratory procedures and solvents previously disclosed for the alkylation of Formula II intermediates with Formula VII phenoxyalkylhalides are operable in addition to alkanols, particularly isopropanol.

The process of Scheme 2 for preparing a compound of Formula (XI) comprises reacting p-toluenesulfonyl chloride (tosyl chloride) with a Formula (XIV) alcohol to provide the tolsylate of Formula (XV) and further reacting the tosylate (XV) with a substituted piperazine (XVI). In converting the tosylate to the triazolone product (XI) the Formula (XVI) substituted piperazine is reacted with the tosylate (XV) by dissolving the tosylate and piperazine nucleophile (1.1 mol eq) in a reaction inert solvent such as methylene chloride employing an acid scavenger such as the organic base N,N-diisopropylethylamine.

In the foregoing formulas of Schemes 1 and 2, "Y, $X_1$, n, $R_2$ and Z" are as previously defined for Formula XI).

The compounds of Formula (XI) are obtained according to methods previously set forth or by modifications illustrated below which are embodied in a unitary process comprising reacting a compound of Formula X'

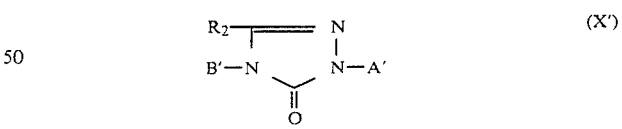

wherein A' is hydrogen or a piperazinyl radical (a)

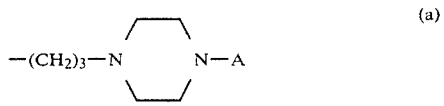

or a radical (b)

$$-(CH_2)_3-X''$$  (b)

wherein X" is a leaving group such as halogen, sulfate, phosphate, mesylate and preferably tosylate; and B' is hydrogen or a radical (c)

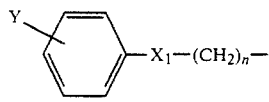
(c)

with an alkylating agent of Formula VII or XIII or a piperazine of Formula XVI when A' is radical (b) and B' is radical (c).

EXAMPLE 8

Preparation of Formula XI Compounds by Alkylating a Formula (XII) Triazolone

Equimolar amounts of the requisite triazolone (XII) and piperazinylpropyl chloride (XIII, X'=Cl), anhydrous pulverized potassium carbonate (3–4 mol eq), tetrabutylammonium hydrogen sulfate (0.1 mol eq) and potassium iodide (0.05 mol eq) are heated at reflux in acetonitrile for a 24–48 hr. period with vigorous stirring while maintaining anhydrous conditions or under a nitrogen atmosphere. Conventional methods such as thin layer chromatography are employed to determine when the reaction is complete. Excess acetonitrile is removed under reduced pressure and the resulting mixture partitioned between water and methylene chloride. The organic extract is dried with sodium carbonate or magnesium sulfate, filtered and concentrated in vacuo to afford the crude product usually as a viscous oil. Purification of the product is carried out by conventional flash chromatography (W. C. Still, et al., *J. Org. Chem.*, 43, 2923 (1978)) with subsequent conversion to a pharmaceutically acceptable salt such as the hydrochloride.

Adaptation of this procedure to 1-(3-chlorophenyl)-4-(3-chloropropyl)piperazine (XIII, X'=Cl, Z=3-chlorophenyl) with the requisite triazolone (XII) provides the Formula XI products indicated.

(a) 2-[3-[4-(3-CHLOROPHENYL)-1-PIPERAZINYL]PROPYL]-5-ETHYL-2,4-DIHYDRO-4-[2-(2-METHOXYPHENOXY)ETHYL]-3H-1,2,4-TRIAZOL-3-ONE HYDROCHLORIDE HYDRATE (XI, Y=2—CH$_3$O, X$_1$=O, n=2, R$_2$=C$_2$H$_5$, Z=3-chlorophenyl). Crystallized from ethyl acetate, m.p. 125°–128° C.

Anal. Calcd. for C$_{26}$H$_{34}$ClN$_5$O$_3$.HCl.0.4H$_2$O: C, 57.44; H, 6.64; N, 12.88. Found: C, 57.28; H, 6.54; N, 13.15.

NMR (DMSO-d$_6$): 1.20 (3,t, 7.4 H$_3$); 2.15 (2,m); 2.76 (2,q, 7.4 H$_z$); 3.20 (8,m); 3.71 (3,s); 3.90 (8,m); 6.89 (7,m); 7.24 (1,m); 11.55 (1,bs).

(b) 2-[3-[4-(3-CHLOROPHENYL)-1-PIPERAZINYL]PROPYL]-5-(1,1-DIMETHYLETHYL)-2,4-DIHYDRO-4-(2-PHENOXYETHYL)-3H-1,2,4-TRIAZOL-3-ONE HYDROCHLORIDE (XI, Y=H, X$_1$=O, n=2, R$_2$=tert-butyl, Z=3-chlorophenyl). Crystallized from ethanol-ether, m.p. 156°–159° C.

Anal. Calcd. for C$_{27}$H$_{36}$ClN$_5$O$_2$.HCl: C, 60.67; H, 6.98; N, 13.10. Found: C, 60.85; H, 6.93; N, 12.79.

NMR (DMSO-d$_6$): 1.36 (9,s); 2.18 (2,m); 3.20 (8,m); 3.72 (4,m); 4.21 (4,m); 6.96 (6,m); 7.24 (3,m); 11.75 (1,bs).

(c) 2-[3-[4-(3-CHLOROPHENYL)-1-PIPERAZINYL]PROPYL]-5-ETHYL-2,4-DIHYDRO-4-[2-(4-METHOXYPHENOXY)ETHYL]-3H-1,2,4-TRIAZOL-3-ONE HYDROCHLORIDE HEMIHYDRATE (XI, Y=4—CH$_3$O, X$_1$=O, n=2, R$_2$=C$_2$H$_5$, Z=3-chlorophenyl). Crystallized from ethanol, m.p. 112°–117° C.

Anal. Calcd. for C$_{26}$H$_{34}$ClN$_5$O$_3$.HCl.0.5H$_2$O: C, 57.25; H, 6.65; N, 12.84; H$_2$O, 1.65. Found: C, 57.51; H, 6.57; N, 12.54; H$_2$O, 1.68.

NMR (DMSO-d$_6$): 1.20 (3,t, 7.2 Hz); 2.16 (2,m); 2.65 (2,q, 7.2 Hz); 3.16 (8,m); 3.67 (3,s); 3.90 (8,m); 6.83 (4,s); 6.95 (3,m);

(d) 2-[3-[4-(3-CHLOROPHENYL)-1-PIPERAZINYL]PROPYL]-5-ETHYL-2,4-DIHYDRO-4-[2-[3-(TRIFLUOROMETHYL)PHENOXY]ETHYL]-3H-1,2,4-TRIAZOL-3-ONE HYDROCHLORIDE HEMIHYDRATE (XI, Y=3—CF$_3$, X$_1$=O, n=2, R$_2$=C$_2$H$_5$, Z=3-chlorophenyl). Crystallized from ethanol-ether, m.p. 142°–144° C.

Anal. Calcd. for C$_{26}$H$_{31}$ClF$_3$N$_5$O$_2$.HCl.0.5H$_2$O: C, 53.52; H, 5.70; N, 12.00; H$_2$O, 1.54. Found: C, 53,35; H, 5.58; N, 11.75; H$_2$O, 1.88.

NMR (DMSO-d$_6$): 1.20 (3,t, 7.2 Hz); 2.17 (2,m); 2.66 (2,q, 7.2 Hz); 3.28 (8,m); 3.72 (9,m); 3.96 (2,t, 5.0 Hz); 4.26 (2,t, 5.0 Hz); 6.89 (3,m); 7.28 (4,m); 7.50 (1,m); 11.60 (1,bs).

(e) 4-[3-(3-CHLOROPHENOXY)PROPYL]-2-[3-[4-(3-CHLOROPHENYL)-1-PIPERAZINYL]PROPYL]-5-ETHYL-2,4-DIHYDRO-3H-TRIAZOL-3-ONE HYDROCHLORIDE (XI, Y=3-Cl, X$_1$=O, n=3, R$_2$=C$_2$H$_5$, Z=3-chlorophenyl). Crystallized from ethanol, m.p. 134°–137° C.

Anal. Calcd. for C$_{26}$H$_{33}$Cl$_2$N$_5$O$_2$.HCl: C, 56.27; H, 6.18; N, 12.62. Found: C, 56.54; H, 6.27; N, 12.67.

NMR (DMSO-d$_6$): 1.16 (3,t, 7.4 Hz); 2.10 (4,m); 2.55 (2,q, 7.4 Hz); 3.20 (8,m); 3.74 (6,m); 4.02 (2,m); 6.95 (6,m); 7.24 (3,m); 11.76 (1,bs).

(f) 4-[2-(3-CHLOROPHENOXY)ETHYL]-2-[3-[4-(3-CHLOROPHENYL)-1-PIPERAZINYL]PROPYL]-5-ETHYL-2,4-DIHYDRO-3H-1,2,4-TRIAZOL-3-ONE HYDROCHLORIDE (XI, Y=3-Cl, X$_1$=O, n=2, R$_2$=C$_2$H$_5$, Z=3-chlorophenyl). Crystallized from ethanol, m.p. 181°–183° C.

Anal. Calcd. for C$_{25}$H$_{31}$Cl$_2$N$_5$O$_2$.HCl: C, 55.51; H, 5.96; N, 12.95. Found: C, 55.73; H, 6.16; N, 12.67.

NMR (DMSO-d$_6$): 1.20 (3,t, 7.2 Hz); 2.18 (2,m); 2.65 (2,q, 7.2 Hz); 3.18 (6,m); 3.72 (6,m); 3.95 (2,t, 5.0 Hz); 4.20 (2,t, 5.0 Hz); 6.98 (6,m); 7.24 (2,m); 11.60 (1,bs).

(g) 2-[3-[4-(3-CHLOROPHENYL)-1-PIPERAZINYL]PROPYL]-5-ETHYL-2,4-DIHYDRO-4-[3-[3-(TRIFLUOROMETHYL)PHENOXY]PROPYL]-3H-1,2,4-TRIAZOL-3-ONE HYDROCHLORIDE (XI, Y=3-CF$_3$, X$_1$=O, n=3, R$_2$=C$_2$H$_5$, Z=3-chlorophenyl). Crystallized from ethanol, m.p. 153°–154° C.

Anal. Calcd. for C$_{27}$H$_{33}$ClF$_3$N$_5$O$_2$.HCl: C, 55.11; H, 5.82; N, 11.90. Found: C, 55.15; H, 5.78; N, 11.95.

NMR (DMSO-d$_6$): 1.17 (3,t, 7.2 Hz); 2.11 (4,m); 2.56 (2,q, 7.2 Hz); 3.20 (8,m); 3.78 (6,m); 4.10 (2,t, 6.0 Hz); 6.95 (3,m); 7.20 (4,m); 7.55 (1,m); 11.75 (1,bs).

(h) 2-[3-[4-(3-CHLOROPHENYL)-1-PIPERAZINYL]PROPYL]-5-ETHYL-2,4-DIHYDRO-4-(3-PHENYLPROPYL)-3H-1,2,4-TRIAZOL-3-ONE HYDROCHLORIDE (XI, Y=H, X$_1$=direct bond, n=3, R$_2$=C$_2$H$_5$, Z=3-chlorophenyl). Crystallized from ethanol, m.p. 176°–177° C.

Anal. Calcd. for C$_{26}$H$_{34}$ClN$_5$O.HCl: C, 61.90; H, 6.99; N, 13.88. Found: C, 61.96; H, 7.01; N, 13.99.

NMR (DMSO-d$_6$): 1.18 (3,t, 7.5 Hz); 2.00 (4,m); 2.60 (4,m); 3.20 (6,m); 3.68 (8,m); 6.92 (3,m); 7.24 (6,m); 11.68 (1,bs).

(i) 2-[3-[4-(3-CHLOROPHENYL)-1-PIPERAZINYL]PROPYL]-5-ETHYL-2,4-DIHYDRO-4-(4-PHENYLBUTYL)-3H-1,2,4-TRIAZOL-3-ONE HYDROCHLORIDE (XI, Y=H, $X_1$=direct bond, n=4, $R_2=C_2H_5$, Z=3-chlorophenyl). Crystallized from ethanol, m.p. 190°–192° C.

Anal. Calcd. for $C_{27}H_{36}ClN_5O \cdot HCl$: C, 62.55; H, 7.20; N, 13.51. Found: C, 62.41; H, 7.24; N, 13.56.

NMR (DMSO-$d_6$): 1.16 (3,t, 7.2 Hz); 1.59 (4,m); 2.15 (2,m); 2.58 (4,m); 3.18 (4,m); 3.60 (10,m); 6.91 (3,m); 7.20 (6,m); 11.70 (1,bs).

(j) 2-[3-[4-(3-CHLOROPHENYL)-1-PIPERAZINYL]PROPYL]-2,4-DIHYDRO-4-(2-PHENOXYETHYL)-3H-1,2,4-TRIAZOL-3-ONE HYDROCHLORIDE (XI, Y=H, $X_1$=O, n=2, $R_2$=H, Z=3-chlorophenyl). Crystallized from ethanol, m.p. 140°–142° C.

Anal. Calcd. for $C_{23}H_{28}ClN_5O_2 \cdot HCl$: C, 57.74; H, 6.11; N, 14.64. Found: C, 57.71; H, 6.10; N, 14.44.

NMR (DMSO-$d_6$): 2.18 (2,m); 3.16 (6,m); 3.49 (2,m); 3.78 (4,m); 3.97 (2,t, 5.0 Hz); 4.20 (2,t, 5.0 Hz); 6.99 (6,m); 7.23 (3,m); 8.06 (1,s); 11.65 (1,bs).

(k) 2-[3-[4-(3-CHLOROPHENYL)-1-PIPERAZINYL]PROPYL]-2,4-DIHYDRO-4-[2-(3-CHLOROPHENOXY)ETHYL]-3H-1,2,4-TRIAZOL-3-ONE HYDROCHLORIDE (XI, Y=3-Cl, $X_1$=O, n=2, $R_2$=H, Z=3-chlorophenyl). Crystallized from ethanol, m.p. 158°–160° C.

Anal. Calcd. for $C_{23}H_{27}Cl_2N_5O_2 \cdot HCl$: C, 53.86; H, 5.50; N, 13.66. Found: C, 54.14; H, 5.40; N, 13.68.

NMR (DMSO-$d_6$): 2.20 (2,m); 3.19 (8,m); 3.69 (4,m); 3.48 (2,m); 4.25 (2,t, 5.0 Hz); 7.02 (8,m); 8.07 (1,s); 11.65 (1,bs).

(l) 4-[3-(3-CHLOROPHENOXY)PROPYL]-2-[3-[4-(3-CHLOROPHENYL)-1-PIPERAZINYL]-PROPYL]-2,4-DIHYDRO-3H-1,2,4-TRIAZOL-3-ONE HYDROCHLORIDE HYDRATE (XI, Y=3-Cl, $X_1$=O, n=3, $R_2$=H, Z=3-chlorophenyl). Crystallized from ethanol, m.p. 140°–144° C.

Anal. Calcd. for $C_{24}H_{29}Cl_2N_5O_2 \cdot 1.4HCl \cdot 0.25H_2O$: C, 52.80; H, 5.71; N, 12.83; $H_2O$, 0.82. Found: C, 52.95; H, 5.63; N, 12.80; $H_2O$, 0.84.

NMR (DMSO-$d_6$): 2.12 (4,m); 3.18 (8,m); 3.75 (6,m); 4.02 (2,t, 6.0 Hz); 6.48 (6,m); 7.24 (2,m); 7.65 (1,bs); 8.04 (1,s); 11.60 (1,bs).

(m) 2-[3-[4-(3-CHLOROPHENYL)-1-PIPERAZINYL]PROPYL]-2,4-DIHYDRO-4-[3-[3-(TRIFLUOROMETHYL)PHENOXY]PROPYL]-3H-1,2,4-TRIAZOL-3-ONE DIHYDROCHLORIDE HYDRATE (XI, Y=3-$CF_3$, $X_1$=O, n=3, $R_2$=H, Z=3-chlorophenyl). Crystallized from ethanol, m.p. 153°–157° C.

Anal. Calcd. for $C_{25}H_{29}ClF_3N_5O_2 \cdot 2HCl \cdot 0.4H_2O$: C, 49.71; H, 5.31; N, 11.59; $H_2O$, 1.19. Found: C, 49.83; N, 5.28; N, 11.45; $H_2O$, 1.14.

NMR (DMSO-$d_6$): 2.14 (4,m); 3.19 (8,m); 3.78 (6,m); 4.10 (2,t, 6.0 Hz); 6.92 (3,m); 7.21 (4,m); 7.52 (1,m); 8.07 (1,s); 9.24 (1.5,bs); 11.65 (1,bs).

EXAMPLE 9

Preparation of Formula XI Compounds by Alkylating a Formula XVI Piperazine

A methylene chloride solution of the requisite triazolone tosylate (XV), 1.1 mol eq of the substituted piperazine (XVI) and N,N-diisopropylethylamine (1.0 mol eq) is maintained at 40°–45° C. for a 24–72 hr. period. The Formula (XI) triazolone product is purified by flash chromatography as free base. Conversion to pharmaceutically acceptable acid addition salts such as the hydrochloride is carried out in a conventional way by dissolving the base in a minimal amount of ethanol and adding ethanolic hydrogen chloride.

Adaptation of this procedure to 2-[3-(p-toluenesulfonate)propyl]-5-ethyl-2,4-dihydro-4-(2-phenoxyethyl)-3H-1,2,4-triazol-3-one obtained according to Example 12 with the requisite substituted piperazine (XVI) provides the Formula XI products indicated.

(a) 2-[3-[4-(1,2-BENZISOTHIAZOL-3-YL)-1-PIPERAZINYL]PROPYL]-5-ETHYL-2,4-DIHYDRO-4-(2-PHENOXYETHYL)-3H-1,2,4-TRIAZOL-3-ONE (XI, Y=H, $X_1$=O, n=2, $R_2=C_2H_5$,

Z = 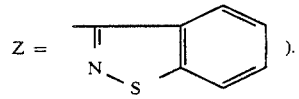 ).

Crystallized from acetone, m.p. 105°–106° C.

Anal. Calcd. for $C_{26}H_{32}N_6O_2S$: C, 63.39; H, 6.55; N, 17.06; S, 6.51. Found: C, 63.19; H, 6.52; N, 16.90; S, 6.61.

NMR (CDCl$_3$): 1.32 (3,t, 7.2 Hz); 1.97 (2,m); 2.53 (2,q, 7.2 Hz); 2.65 (6,m); 3.54 (4,m); 3.84 (2,t, 7.0 Hz); 4.10 (4,m); 6.89 (3,m); 7.26 (4,m); 7.84 (2,m).

(b) 2-[4-[3-[3-ETHYL-4,5-DIHYDRO-5-OXO-4-(2-PHENOXYETHYL)-1H-TRIAZOL-1-YL]PROPYL]-1-PIPERAZINYL]-3-PYRIDINECARBONITRILE HYDROCHLORIDE HYDRATE (XI, Y=H, $X_1$=O, n=2, $R_2=C_2H_5$,

Z = 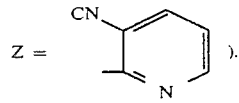 ).

Crystallized from ethanol, m.p. 159°–161° C.

Anal. Calcd. for $C_{25}H_{31}N_7O_2 \cdot HCl \cdot 0.25H_2O$: C, 59.74; H, 6.53; N, 19.51; Cl, 7.05. Found: C, 59.74; H, 6.44; N, 19.80; Cl, 7.09.

NMR (DMSO-$d_6$): 1.20 (3,t, 7.4 Hz); 2.14 (2,m); 2.67 (2,q, 7.4 Hz); 3.15 (6,m); 3.64 (6,m); 4.15 (4,m); 6.95 (4,m); 7.29 (2,m); 8.17 (1,dd, 1.8 Hz, 7.2 Hz); 8.50 (1,dd, 1.8 Hz, 4.8 Hz); 11.88 (1,bs).

(c) 5-ETHYL-2,4-DIHYDRO-4-(2-PHENOXYETHYL)-2-[3-[4-(PHENYLMETHYL)-1-PIPERAZINYL]PROPYL]-3H-1,2,4-TRIAZOL-3-ONE DIHYDROCHLORIDE (XI, Y=Y, $X_1$=O, n=2, $R_2=C_2H_5$, Z=—$CH_2C_6H_5$). Crystallized from ethanol, m.p. 214°–215° C.

Anal. Calcd. for $C_{26}H_{35}N_5O_2 \cdot 2HCl$: C, 59.77; H, 7.14; N, 13.40. Found: C, 59.82; H, 7.12; N, 13.25.

NMR (DMSO-$d_6$): 1.19 (3,t, 7.4 Hz); 2.10 (2,m); 2.65 (2,q, 7.4 Hz); 3.17 (2,m); 3.52 (10,m); 3.95 (2,t, 5.0 Hz); 4.16 (2,t, 5.0 Hz); 4.40 (2s); 6.94 (3,m); 7.46 (7,m).

(d) 5-ETHYL-2,4-DIHYDRO-4-(2-PHENOXYETHYL)-2-[3-[4-(QUINOLIN-2-YL)-1-PIPERAZINYL]PROPYL]-3H-1,2,4-TRIAZOL-3-ONE DIHYDROCHLORIDE (XI, Y=H, $X_1$=O, n=2, $R_2=C_2H_5$,

Z = 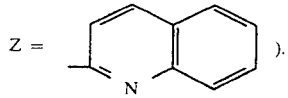.

Crystallized from ethanol, m.p. 208° C. (dec.).

Anal. Calcd. for $C_{28}H_{34}N_6O_2 \cdot 2HCl$: C, 60.10; H, 6.49; N, 15.02. Found: C, 60.02; H, 6.52; N, 14.96.

NMR (DMSO-$d_6$): 1.20 (3,t, 7.4 Hz); 2.19 (2,m); 2.66 (2,q, 7.4 Hz); 3.20 (4,m); 3.75 (6,m); 3.98 (2,m); 4.18 (2,m); 4.97 (2,m); 6.93 (3,m); 7.30 (2,m); 7.75 (4,m); 8.52 (2,m).

(e) 2-[3-[4-(3-CHLORO-4-FLUOROPHENYL)-1-PIPERAZINYL]PROPYL]-5-ETHYL-2,4-DIHYDRO-4-(2-PHENOXYETHYL)-3H-1,2,4-TRIAZOL-3-ONE HYDROCHLORIDE HEMIHYDRATE (XI, Y=H, $X_1$=O, n=2, $R_2$=$C_2H_5$,

Z = 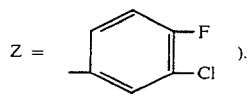.

Crystallized from ethanol, m.p. 171° C. (dec.).

Anal. Calcd. for $C_{25}H_{31}ClFN_5O_2 \cdot HCl \cdot 0.5H_2O$: C, 56.29; H, 6.24; N, 13.13; $H_2O$, 1.69. Found: C, 56.58; H, 6.22; N, 13.11; $H_2O$, 1.61.

NMR (DMSO-$d_6$): 1.21 (3,t, 7.2 Hz); 2.18 (2,m); 2.68 (2,q, 7.2 Hz); 3.20 (4,m); 3.45 (4,m); 3.74 (4,m); 3.98 (2,t, 5.0 Hz); 4.19 (2,t, 5.0 Hz); 6.97 (4,m); 7.25 (9,m); 12.00 (1,bs).

(f) 5-ETHYL-2,4-DIHYDRO-4-(2-PHENOXYETHYL)-2-[3-[4-[3-(TRIFLUOROMETHYL)-PHENYL]-1-PIPERAZINYL]PROPYL]-3H-1,2,4-TRIAZOL-3-ONE HYDROCHLORIDE (XI, Y=H, $X_1$=O, n=2, $R_2$=$C_2H_5$,

Z = 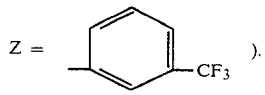.

Crystallized from ethanol, m.p. 169°-171° C.

Anal. Calcd. for $C_{26}H_{32}F_3N_5O_2 \cdot HCl$: C, 57.83; H, 6.16; N, 12.97. Found: H, 57.87; H, 6.20; N, 12.62.

NMR (DMSO-$d_6$): 1.21 (3,t, 7.4 Hz); 2.20 (2,m); 2.68 (2,q, 7.4 Hz); 3.24 (8,m); 3.90 (6,m); 4.19 (2,t, 5.0 Hz); 6.97 (3,m); 7.28 (6,m); 11.75 (1,bs).

(g) 2-[3-[4-(2-CHLORO-6-PYRAZINYL)-1-PIPERAZINYL]PROPYL]-5-ETHYL-2,4-DIHYDRO-4-(2-PHENOXYETHYL)-3H-1,2,4-TRIAZOL-3-ONE HYDROCHLORIDE (XI, Y=H, $X_1$=O, n=2, $R_2$=$C_2H_5$,

Z = 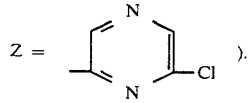.

Crystallized from ethanol, m.p. 194°-196° C.

Anal. Calcd. for $C_{23}H_{30}ClN_7O_2 \cdot HCl$: C, 54.33; H, 6.15; N, 19.28. Found: C, 54.17; H, 6.17; N, 19.38.

NMR (DMSO-$d_6$): 1.20 (3,t, 7.2 Hz); 2.19 (2,m); 2.67 (2,q, 7.2 Hz); 3.11 (4,m); 3.62 (6,m); 4.18 (6,m); 6.92 (3,m); 7.28 (2,m); 7.94 (1,s); 8.39 (1,s); 11.90 (1,bs).

(h) 2-[3-[4-(6-CHLORO-2-PYRIDINYL)-1-PIPERAZINYL]PROPYL]-5-ETHYL-2,4-DIHYDRO-4-(2-PHENOXYETHYL)-3H-1,2,4-TRIAZOL-3-ONE HYDROCHLORIDE (XI, Y=H, $X_1$=O, n=2, $R_2$=$C_2H_5$,

Z = 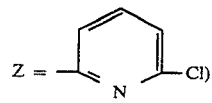

Crystallized from ethanol-ether, m.p. 191°-192° C.

Anal. Calcd. for $C_{24}H_{31}ClN_6O_2 \cdot HCl$: C, 56.80; H, 6.36; N, 16.56. Found: C, 56.41; H, 6.39; N, 16.77.

NMR (DMSO-$d_6$): 1.20 (3,t, 7.5 Hz); 2.16 (2,m); 2.66 (2,q, 7.5 Hz); 3.10 (4,m); 3.42 (4,m); 3.72 (2,m); 3.95 (3,m); 4.16 (3,m); 6.91 (5,m); 7.27 (2,m); 7.61 (1,t, 8.0 Hz); 11.65 (1,bs).

(i) XI, Y=H, $X_1$=O, n=2, $R_2$=$C_2H_5$,

Z = 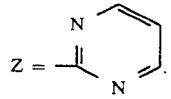.

(j) XI, Y=H, $X_1$=O, n=2, $R_2$=$C_2H_5$,

Z = 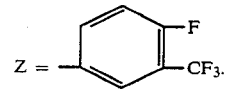.

EXAMPLE 10

Preparation of Triazolones of Formula (XII)

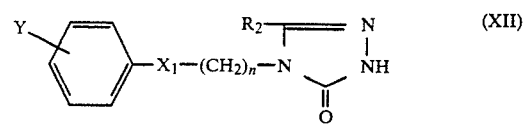

The Formula (XII) triazolones wherein $R_2$ is lower alkyl can be prepared as follows:

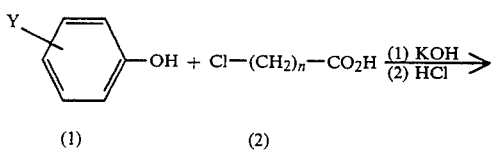

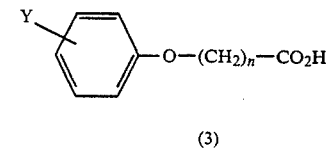

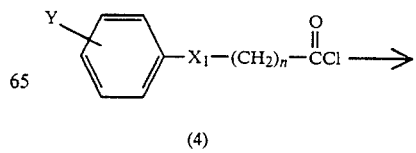

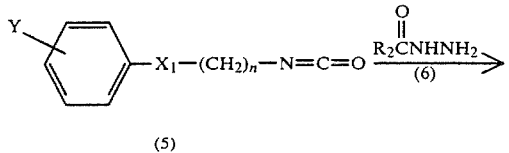

(5)

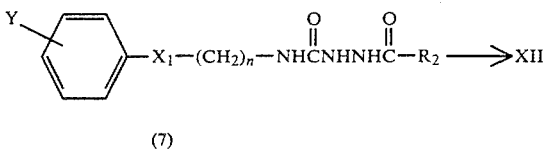

(7)

An aqueous solution of the potassium salt of the phenol (1) is combined with an aqueous solution of the potassium salt of 3-chloropropionic acid (2). The resulting solution is heated at reflux for 10 min. and then cooled to 0° C. and concentrated hydrochloric acid added to pH 2. The acidic solution is extracted with chloroform and the chloroform extract is treated with saturated aqueous sodium bicarbonate. The bicarbonate phase is acidified to pH 2 with concentrated hydrochloric acid precipitating phenoxy acid (3). The phenoxy acid (3) is converted to the acid chloride by reaction with thionyl chloride (2 mol eq) in chloroform at reflux temperature. Excess thionyl chloride and chloroform are removed under reduced pressure and the acid chloride used without further purification. Phenylalkanoyl chlorides are similarly prepared and both types are embodied in (4) wherein $X_1$ represents oxygen or a direct bond.

Acid chloride (4) is converted to the isocyanate by the procedure of Washburne, et al., Synthetic Comm., 2, 227 (1972) employing toluene as a solvent. The reaction mixture is concentrated under reduced pressure and residual isocyanate used without further purification. The isocyanate is dissolved in methylene chloride and added to a well stirred and cooled (0° C.) methylene chloride solution containing a hydrazide (6) to provide the semicarbazide (7) which is purified by removing the methylene chloride under reduced pressure and flash chromatographing residual oil.

Intramolecular cyclization of the semicarbazide (7) by treatment with aqueous potassium hydroxide (5 mol eq of 10% soln) and heating at 100° C. for a 5 hr. period affords the triazolone of Formula (XII) wherein $R_2$ is lower alkyl.

The Formula (XII) triazolones wherein $R_2$ is hydrogen can be prepared by reacting the isocyanate (5) with tert.-butyl carbazate in methylene chloride at 0° C. to provide the tert.-butylcarboxy semicarbazide (8) which treated with a saturated HCl methanolic solution provides the semicarbazide (9). Reaction of (9) with excess triethylorthoformate at reflux temperature affords the Formula (XII) triazolones wherein $R_2$ is H.

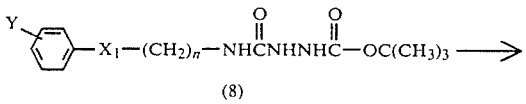

(8)

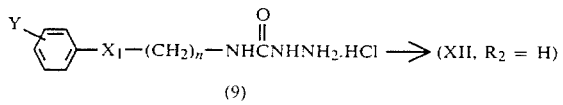

(9)

Adaptation of the foregoing procedures provides the following Formula (XII) triazolones.

(a) $Y=2\text{-}CH_3O$, $X_1=0$, $n=2$, $R_2=C_2H_5$.
Crystallized from methylene chloride, m.p. 141°–142° C.
Anal. Calcd. for $C_{13}H_{17}N_3O_3$: C, 59.30; H, 6.51; N, 15.96. Found: C, 59.23; H, 6.55; N, 16.01.

(b) $Y=H$, $X_1=0$, $n=2$, $R_2=\text{tert.-butyl}$.
Crystallized from ethyl acetate-hexane.
Anal. Calcd. for $C_{14}H_{19}N_3O_2$: C, 64.35; H, 7.33; N, 16.08. Found: C, 64.25; H, 7.40; N, 15.42.

(c) $Y=4\text{-}CH_3O$, $X_1=0$, $n=2$, $R_2=C_2H_5$.
Crystallized from acetone.
Anal. Calcd. for $C_{13}H_{17}N_3O_3$: C, 59.30; H, 6.51; N, 15.96. Found: C, 59.51; H, 6.44; N, 15.16.

(d) $Y=3\text{-}CF_3$, $X_1=0$, $n=2$, $R_2=C_2H_5$.
Crystallized from ethanol-water.
Anal. Calcd. for $C_{13}H_{14}F_3N_3O_2$: C, 51.83; H, 4.68; N, 13.95. Found: C, 51.95; H, 4.65; N, 13.91.

(e) $Y=3\text{-}Cl$, $X_1=0$, $n=3$, $R_2=C_2H_5$.
m.p. 120°–124° C.

(f) $Y=3\text{-}Cl$, $X_1=0$, $n=2$, $R_2=C_2H_5$.
(g) $Y=3\text{-}CF_3$, $X_1=0$, $n=3$, $R_2=C_2H_5$.
(h) $Y=H$, $X_1=\text{direct bond}$, $n=3$, $R_2=C_2H_5$.
(i) $Y=H$, $X_1=\text{direct bond}$, $n=4$, $R_2=C_2H_5$.
(j) $Y=H$, $X_1=0$, $n=2$, $R_2=H$.
Crystallized from ethanol-water.
Anal. Calcd. for $C_{10}H_{11}N_3O_2$: C, 58.52; H, 5.41; N, 20.48. Found: C, 58.76; H, 5.36; N, 20.48.

(k) $Y=3\text{-}Cl$, $X_1=0$, $n=2$, $R_2=H$.
(l) $Y=3\text{-}Cl$, $X_1=0$, $n=3$, $R_2=H$.
(m) $Y=3\text{-}CF_3$, $X_1=0$, $n=3$, $R_2=H$.

EXAMPLE 11

Preparation of Piperazine Reactants

Appropriate piperazine reactants XIII and XVI employed in the process of the present invention are obtained in accordance with standard synthetic procedures employed by those skilled in the art for preparation of similar type compounds. C. B. Pollard, et al., J. Org. Chem., 24, 764–767 (1959), Palazzo, et al., U.S. Pat. No. 3,381,009 and Wu, et al., U.S. Pat. No. 3,717,634 all describe methods applicable for the preparation of such compounds and the aforementioned patents are incorporated herein by reference. By application of these methods or other conventional methods, the following representative piperazine reactants are obtained.

(a) 3-(1-PIPERAZINYL)-1,2-BENZOISOTHIAZOLE

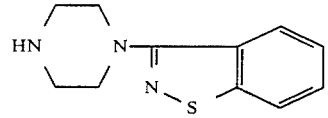

A mixture of 3-chloro-1,2-benzisothiazole (37.8 g., 0.235 mole) and piperazine (304.2 g., 3.53 mole) is heated under an argon atmosphere for a period of 20 hr. at 120° C. in a closed reactor. The reaction mixture is dissolved in 2 liters of water and the aqueous solution repeatedly extracted with methylene chloride. Extracts are combined, dried over magnesium sulfate and concentrated in vacuo. Residual material is taken up in ether, filtered and concentrated in vacuo to afford 24.4 g. (47%) of 3-(1-piperazinyl)-1,2-benzisothiazole free base as a viscous oil.

A sample of the free base converted to the hydrochloride salt in ether with ethanolic hydrogen chloride and crystallized from methanol-ethanol affords analytically pure 3-(1-piperazinyl)-1,2-benzisothiazole hydrochloride, m.p. 280° C. (dec.).

Anal. Calcd. for $C_{11}H_{13}N_3S \cdot HCl$: C, 51.66; H, 5.52; N, 16.43. Found: C, 51.34; H, 5.46; N, 16.16.

(b) N-(2-CHLORO-6-PYRAZINYL)PIPERAZINE

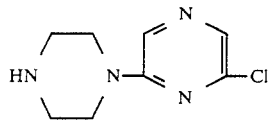

A mixture of 2,6-dichloropyrazine (5.0 g., 33.6 mmol), N-(ethoxycarbonyl)piperazine (5.57 g., 35.2 mmol) and potassium carbonate (13.9 g., 100.7 mmol) in acetonitrile is refluxed for a 24 hr. period. Insolubles are collected and the filtrate concentrated under reduced pressure. Crystallization of residual material from hexane affords N-(2-chloro-6-pyrazinyl)-1-ethoxycarbonyl-piperazine.

Anal. Calcd. for $C_{11}H_{15}ClN_4O_2$: C, 48.80; H, 5.59; N, 20.70. Found: C, 48.62; H, 5.59; N, 20.70.

The carbethoxy protecting group is removed by treating the foregoing compound with HCl to afford 4-(2chloro-6-pyrazinyl)piperazine hydrochloride.

Anal. Calcd. for $C_8H_{11}ClN_4 \cdot HCl$: C, 40.87; H, 5.14; N, 23.83. Found: C, 41.05; H, 5.22; N, 23.68.

(c) N-(3-CHLORO-4-FLUOROPHENYL)PIPERAZINE

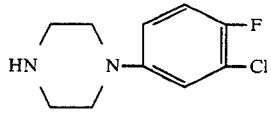

A xylene (20 ml.) solution of 3-chloro-4-fluoroaniline (5.0 g., 34.3 mmol) and bis-(2-chloroethyl)amine hydrochloride (6.13 g., 34.3 mmol) is heated to reflux for 64 hrs. The mixture is extracted with warm water and the aqueous phase then extracted with methylene chloride. The aqueous phase is made basic with 50% sodium hydroxide and extracted with methylene chloride which is dried over potassium carbonate and concentrated under reduced pressure. Residual material is distilled and the fraction having a b.p. of about 100° C. at 0.25 mmHg collected. Conversion of the amine to the hydrochloride salt and crystallization from ethanol affords N-(3-chloro-4-fluorophenyl)piperazine.

Anal. Calcd. for $C_{10}H_{12}ClFN_2$: C, 55.95; H, 5.63; N, 13.05. Found: C, 56.26; H, 5.62; N, 12.99.

(d) N-(3-TRIFLUOROMETHYLPHENYL)PIPERAZINE

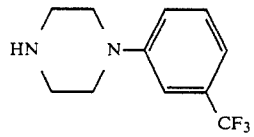

Reaction of 3-trifluoroaniline with bis-(2-chloroethyl)amine hydrochloride in xylene according to (c) above affords the title amine.

Anal. Calcd. for $C_{11}H_{13}F_3N_2$: C, 57.39; H, 5.69; N, 12.17. Found: C, 56.62; H, 5.60; N, 11.69.

(e) N-(6-CHLORO-2-PYRIDINYL)PIPERAZINE

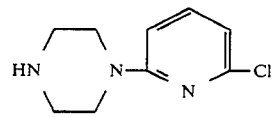

Reaction of 2,6-dichloropyridine with N-(ethoxycarbonyl)piperazine according to (b) above affords the title amine as the hydrochloride.

Anal. Calcd. for $C_9H_{12}ClN_3 \cdot HCl$: C, 46.17; H, 5.60; N, 17.95. Found: C, 46.26; H, 5.64; N, 17.72.

(f) 2-CHLOROPYRIMYRIMIDIN-4-YLPIPERAZINE

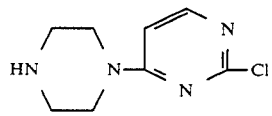

Reaction of 2,6-dichloropyrimidine and piperazine according to (a) above and chromatographic purification affords the title amine.

(g) N(2-QUINOLINYL)PIPERAZINE

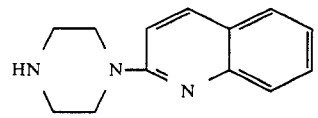

Reaction of piperazine with 2-chloroquinoline as set forth in (a) above provides the title amine.

(h) 2-(PYRIMIDINYL)PIPERAZINE

EXAMPLE 12

Preparation of Triazolone Intermediates of Formulas XIV and XV

The product of Example 5 "5-ethyl-4-(2-phenoxyethyl)-2H-1,2,4-triazol-3(4H)-one" (5.0 g., 23.5 mmol), chloropropanol (2.44 g., 25.8 mmol) and potassium carbonate (9.72 g., 70.4 mmol) in 50 ml. of acetonitrile is heated to reflux for a period of 48 hr. with stirring. Water (50 ml.) is added and the mixture extracted with methylene chloride which is dried over magnesium sulfate and concentrated under reduced pressure to afford 2-(3-hydroxypropyl)-5-ethyl-2,4-dihydro-4-(2-phenoxyethyl)-3H-1,2,4-triazol-3-one (XIV, Y=H, $X_1=O$, n=2, $R_2=C_2H_5$). Purification is carried out by flash chromatography with ethyl acetate.

Anal. Calcd. for $C_{15}H_{21}N_3O_3$: C, 61.84; H, 7.26; N, 14.42. Found: C, 61.61; H, 7.37; N, 14.19.

The alcohol is converted to the tosylate by dissolving in methylene chloride containing N,N-dimethyl-4-aminopyridine (0.05 mol eq) and triethylamine (1.05 mol eq) and treating with tosyl chloride (1.1 mole eq) added in one portion at 0° C. with stirring. After standing for about 24 hr. at 0° C., the mixture is treated with water and extracted several times with methylene chloride. The combined methylene chloride extracts are dried over magnesium sulfate, filtered and concentrated under reduced pressure. Flash chromatography of residual material affords 2-[3-(p-toluenesulfonate)propyl]-5-ethyl-2,4-dihydro-4-(2-phenoxyethyl)-3H-1,2,4-triazol-3-one (XV, Y=H, X$_1$=O, n=2, R$_2$=C$_2$H$_5$).

EXAMPLE 13

2-[3-[4-(3-Chlorophenyl)-1,2,3,6-tetrahydro-1-pyridinyl]propyl]-5-ethyl-2,4-dihydro-4-(2-phenoxyethyl)-3H-1,2,4-triazol-3-one

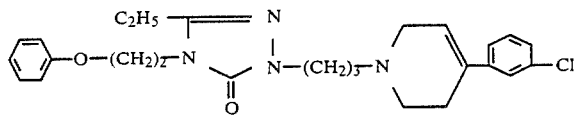

Reaction of 2-[3-(p-toluenesulfonate)propyl]-5-ethyl-2,4-dihydro-4-(2-phenoxyethyl)-3H-1,2,4-triazol-3-one (XV, Y=H, X$_1$=O, n=2, R$_2$=C$_2$H$_5$) with 4-(3-chlorophenyl)-1,2,3,6-tetrahydropyridine according to the procedure of Example 9 provides 2-[3-[4-(3-chlorophenyl)-1,2,3,6-tetrahydro-1-pyridinyl]propyl]-5-ethyl-2,4-dihydro-4-(2-phenoxyethyl)-3H-1,2,4-triazol-3-one hydrochloride. Crystallized from ethanol, m.p. 163°-165° C.

Anal. Calcd. for C$_{26}$H$_{31}$ClN$_4$O$_2$.HCl: C, 62.03; H, 6.41; N, 11.13. Found: C, 61.73; H, 6.39; N, 11.06.

NMR (DMSO-d$_6$): 1.21 (3,t, 7.4 Hz); 2.20 (2,m); 2.67 (2,q, 7.4 Hz); 2.80 (2,m); 3.20 (4,m); 3.80 (6,m); 4.19 (2,t, 5.0 Hz); 6.22 (1,m); 6.95 (3,m); 7.38 (6,m); 11.60 (1,bs).

EXAMPLE 14

5-[3-[4-(3-Chlorophenyl)-1-piperazinyl]propyl]-4-ethyl-2,4-dihydro-2-(2-phenoxyethyl)-3H-1,2,4-triazol-3-one Hydrochloride

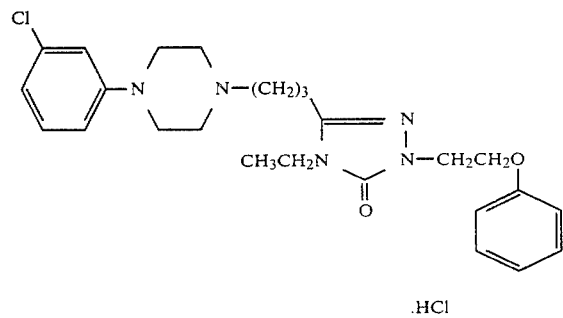

(a) Ethyl 4-[4-(3-Chlorophenyl)piperazin-1-yl]butyrate: Ethyl 4-bromobutyrate (19.5 g, 0.10 mole); m-chlorophenylpiperazine (19.6 g., 0.10 mole); potassium carbonate (4.2 g., 0.04 mole); and a catalytic amount of potassium iodide were refluxed in 200 ml. acetonitrile for about 28 hrs. The reaction mixture was cooled, filtered, and concentrated to a crude oil which was partitioned between methylene chloride and water. The organic layer was washed two times with water, dried (MgSO$_4$), and concentrated in vacuo to about 30 g. of a light brown solid. This material was purified using preparatory high pressure liquid chromatography. A silica gel column was used and was eluted using a mixed solvent comprised of hexane-ethyl acetatemethylene chloride in a ratio of 4.5:4.5:1. The eluent was concentrated to an oil, distilled (Kugelrohr) at approximately 160° at 0.4 Torr. to give 12.6 g. (41%) of yellow oil. This crude ester product was used without further purification.

(b) 4-(3-Chlorophenyl)piperazin-1-ylbutanoic Acid Hydrazide: Crude ethyl 4-[4-(3-chlorophenyl)piperazin-1-yl]butyrate (prepared above in (a), 9.9 g., 0.03 mole) in 20 ml. ethanol was added under a nitrogen atmosphere to a cold stirred solution of anhydrous hydrazine (1.1 g., 0.035 mole) in 5 ml. absolute ethanol. When addition was completed, the reaction was refluxed for 7 days using IR to monitor reaction progress while observing disappearance of the C=O stretching frequency at 1730 cm$^{-1}$. A reaction oil, obtained by concentration in vacuo was partitioned between ether and water. The water layer was extracted three times with additional ether; the ether portions all combined and dried (MgSO$_4$) and concentrated in vacuo to approximately 10 g. of the crude hydrazide product which was used without further purification.

(c) A portion of the hydrazide (prepared above in (b), 4.9 g., 0.016 mole) in 50 mL methylene chloride was added to a cold solution of ethyl isocyanate (1.2 g., 0.016 mole) in 50 ml methylene chloride. The cold reaction solution was stirred for 1 hr. and then concentrated in vacuo affording a theoretical yield of the crude ethyl semicarbazate which was combined with 4.6 g. KOH in 100 ml. water and refluxed for approximately 5 hrs. The reaction mixture was then cooled and the pH adjusted to 8 using 6N HCl. This solution was extracted three times with ether, the ether portions combined and dried (K$_2$CO$_3$) and concentrated in vacuo to yield 4 g. (72%) of the crude 1,2,4-triazol-3-one as a white solid.

This triazolone intermediate product was combined with 1-bromo-2-phenoxyethane (2.5 g., 0.01 mole); potassium carbonate (4.6 g., 0.03 mole) and a catalytic amount of potassium iodide in 150 ml. acetonitrile. This reaction mixture was refluxed for approximately three days during which time small amounts of the phase transfer catalyst tetrabutylammonium hydrogen sulfate (TBAHS, 0.035 g., 0.1 mole) and an additional equivalent of K$_2$CO$_3$ were added. At this point monitoring of the reaction by TLC indicated its completeness. The reaction mixture was cooled, filtered, and concentrated to an oil which was partitioned between methylene chloride and water. The water layer was extracted twice with additional methylene chloride, the methylene chloride portions combined and dried (MgSO$_4$) and concentrated to approximately 5 g. of crude material. This crude material was purified by flash chromatography utilizing a silica column and eluting with methanol (4%)-methylene chloride (96%). Concentration in vacuo gave a yellow oil which was converted to the hydrochloride salt by treatment with ethanolic HCl. Recrystallization from ethanol gave 2.7 g. (49%) white solid, m.p. 153°-155°.

Anal. Cacld. for C$_{25}$H$_{32}$ClN$_5$O$_2$.HCl: C, 59.29; H, 6.57; N, 13.83. Found: C, 59.40; H, 6.55; N, 13.92.

NMR (DMSO-d$_6$): 1.16 (3,t, 7.0 Hz); 2.15 (2,m); 2.70 (2,t, 6.8 Hz); 3.20 (4,m); 3.58 (8,m); 4.00 (2,t, 5.0 Hz); 4.25 (2,t, 5.0 Hz); 6.91 (6,m); 7.27 (3,m); 11.60 (1,bs).

EXAMPLE 15

5-[3-[4-(3-Chlorophenyl)-1-piperazinyl]propyl]2,4-dihydro-4-(2-phenoxyethyl)-3H-1,2,4-triazol-3-one

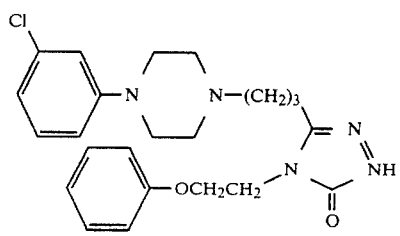

(a) 2-Phenoxyethyl isocyanate:

3-Phenoxypropionic acid (3.0 g., 0.02 mole) was dissolved in 10 ml. of methylene chloride containing a catalytic amount of dimethylformamide. Thionyl chloride (2.7 ml., 0.04 mole) was added under a nitrogen atmosphere in a single portion at ambiant temperature. After being allowed to stand and react for 2 hrs., the reaction mixture was concentrated in vacuo to yield 3.3 g. (100%) of the crude acid chloride product.

The crude acid chloride (3.3 g., 0.02 mole) was dissolved in 2 ml. toluene and heated to 100° whereupon azidotrimethylsilane (2.1 g., 2.4 ml., 0.02 mole) in 2 ml. of toluene was added dropwise at such a rate that nitrogen evolution remained controlled. The reaction was monitored by IR for disappearance of the C=O stretching mode at 1800 cm$^{-1}$ and was complete after about 4-6 hrs. The solvent and excess reagent were distilled under reduced pressure affording the brown-orange isocyanate which was used without further purification in the next step.

Note: While 3-phenoxypropionic acid is commercially available, it can also be conveniently prepared by alkylation of phenol with ethyl 3-bromopropionate followed by ester hydrolysis to give the desired intermediate, 3-phenoxypropionic acid.

(b) 4-(3-Chlorophenyl)-1-piperazinebutanoic Acid Phenoxyethylsemicarbazide:

4-(3-Chlorophenyl)-1-piperazinebutanoic acid hydrazide (prepared above in Example 14, 4.5 g., 0.015 mole) in 100 ml. methylene chloride at 0° was treated with the crude phenoxyethyl isocyanate prepared above in (a). After being stirred at 0° for about 15 min., the reaction mixture was allowed to warm to room temperature and stand overnight. Concentration in vacuo and drying gave 7.6 g. of brown solid product. This crude solid was purified by flash chromatography through a silica column eluting with 15% methanol-methylene chloride to yield 5 g. (61%) semicarbazide product.

(c) The semicarbazide intermediate (prepared above in (b), 5.0 g., 0.01 mole) was refluxed overnight in 60 ml. of 5% KOH solution. Following reaction, this mixture was cooled, neutralized (pH 7) with 6N HCl. Thorough extraction with methylene chloride-ether followed by drying (MgSO$_4$) and concentration of the extracts gave 4.4 g. (91%) of crude 1,2,4-triazol-3-one product. Recrystallization from ethanol gives the pure product as white crystals, m.p. 159°-161°.

Anal. Calcd. for $C_{23}H_{28}ClN_5O_2$: C, 62.51; H, 6.39; N, 15.85. Found: C, 62.35; H, 6.34; N, 15.57.

NMR (DMSO-d$_6$): 1.83 (2,m); 2.50 (8,m); 3.11 (4,m); 3.92 (2,t, 5.0 Hz); 4.15 (2,t, 5.0 Hz); 6.90 (6,m); 7.20 (3,m); 11.38 (1,s).

EXAMPLE 16

5-[3-[4-(3-Chlorophenyl)-1-piperazinyl]propyl]-2-ethyl-2,4-dihydro-4-(2-phenoxyethyl)-3H-1,2,4-triazol-3-one Hydrochloride Hydrate

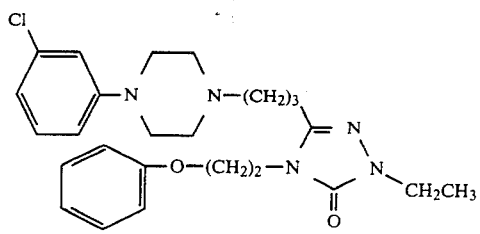

.HCl.½H$_2$O

5-[3-[4-(3-Chlorophenyl)-1-piperazinyl]propyl]-2,4-dihydro-4-(2-phenoxyethyl)-3H-1,2,4-triazol-3-one (prepared above in Example 15, 3.9 g., 0.01 mole); ethyl bromide (1.1 g., 0.75 ml., 0.01 mole); potassium carbonate (3.7 g., 0.03 mole) and a catalytic amount of potassium iodide were dissolved in 250 ml. acetonitrile and refluxed for several days. The reaction was monitored using thin layer chromatography (TLC) to observe the disappearance of the starting triazolone. An additional 0.5 equivalent of the ethyl bromide was added and refluxing continued for a total of five days. At this point, no starting triazolone was observed by TLC. The reaction mixture was cooled, filtered, concentrated in vacuo and partitioned between methylene chloride and water. The water layer was extracted with methylene chloride, the methylene chloride portions combined and dried (MgSO$_4$) and concentrated to 4.1 g. yellow oil. This oil was purified by flash chromatography through a silica gel column eluting with 6% methanol-methylene chloride. Concentration of the eluent yielded 2.8 g. orange oil which was converted to the hydrochloride salt by treatment with ethanolic HCl to afford 1.9 g. white solid, m.p. 150°-153°.

Anal. Calcd. for $C_{25}H_{32}ClN_5O_2$.HCl.½H$_2$O: C, 58.59; H, 6.62; N, 13.67. Found: C, 58.68; H, 6.59; N, 13.36.

NMR (DMSO-d$_6$): 1.20 (3,t, 7.0 Hz); 2.18 (2,m): 2.78 (2,t, 6.8 Hz); 3.30 (8,m); 3.70 (4,m); 3.96 (2,t, 5.0 Hz); 4.17 (2,t, 5.0 Hz); 7.00 (6,m); 7.28 (3,m); 11.05 (1,bs).

What is claimed is:

1. A compound of Formula XI

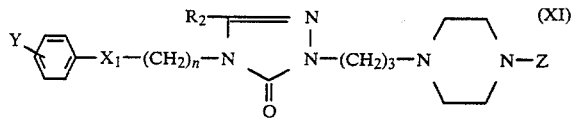

wherein n is 2-4;

R$_2$ is hydrogen or lower alkyl;

X$_1$ is oxygen or a direct bond;

Y is hydrogen, halogen, lower alkoxy or CF$_3$ with the proviso that when Y is hydrogen, n cannot be 2, R$_2$ cannot be ethyl, X$_1$ cannot be oxygen and Z cannot be phenyl having a mono halogen substituent;

Z is benzyl or a radical selected from the group

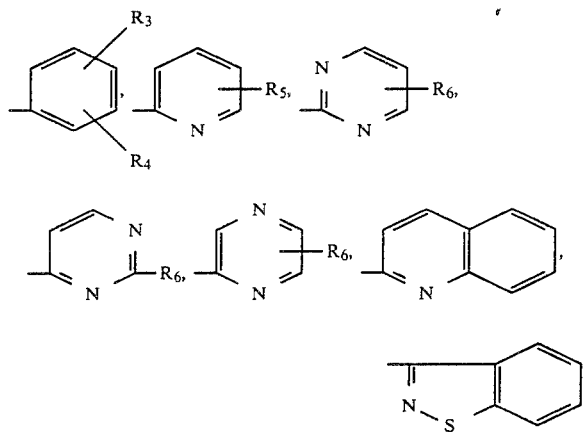

wherein

R₃ is hydrogen or halogen;
R₄ is halogen or CF₃;
R₅ is hydrogen, halogen or cyano;
R₆ is hydrogen or halogen;

or a pharmaceutically acceptable acid addition salt thereof.

2. The compound of claim 1 which is 2-[3-[4-(3-chlorophenyl)-1-piperazinyl]propyl]-5-ethyl-2,4-dihydro-4-(3-phenoxypropyl)-3H-1,2,4-triazol-3-one.

3. The compound of claim 1 which is 2-[3-[4-(3-chlorophenyl)-1-piperazinyl]propyl]-5-ethyl-2,4-dihydro-4-(4-phenoxybutyl)-3H-1,2,4-triazol-3-one.

4. The compound of claim 1 which is 2-[3-[4-(3-chlorophenyl)-1-piperazinyl]propyl]-5-ethyl-2,4-dihydro-4-[2-(2-methoxyphenoxy)ethyl]-3H-1,2,4-triazol-3-one.

5. The compound of claim 1 which is 2-[3-[4-(3-chlorophenyl)-1-piperazinyl]propyl]-5-(1,1-dimethylethyl)-2,4-dihydro-4-(2-phenoxyethyl)-3H-1,2,4-triazol-3-one.

6. The compound of claim 1 which is 2-[3-[4-(3-chlorophenyl)-1-piperazinyl]propyl]-5-ethyl-2,4-dihydro-4-[2-(4-methoxyphenoxy)ethyl]-3H-1,2,4-triazol-3-one.

7. The compound of claim 1 which is 2-[3-[4-(3-chlorophenyl)-1-piperazinyl]propyl]-5-ethyl-2,4-dihydro-4-[2-[3-trifluoromethyl)phenoxy]ethyl]-3H-1,2,4-triazol-3-one.

8. The compound of claim 1 which is 4-[3-(3-chlorophenoxy)propyl]-2-[3-[4-(3-chlorophenyl)-1-piperazinyl]propyl]-5-ethyl-2,4-dihydro-3H-triazol-3-one.

9. The compound of claim 1 which is 4-[2-(3-chlorophenoxy)ethyl]-2-[3-[4-(3-chlorophenyl)-1-piperazinyl]propyl]-5-ethyl-2,4-dihydro-3H-1,2,4-triazol-3-one.

10. The compound of claim 1 which is 2-[3-[4-(3-chlorophenyl)-1-piperazinyl]propyl]-5-ethyl-2,4-dihydro-4-[3-[3-(trifluoromethyl)phenoxy]propyl]-3H-1,2,4-triazol-3-one.

11. The compound of claim 1 which is 2-[3-[4-(3-chlorophenyl)-1-piperazinyl]propyl]-5-ethyl-2,4-dihydro-4-(3-phenylpropyl)-3H-1,2,4-triazol-3-one.

12. The compound of claim 1 which is 2-[3-[4-(3-chlorophenyl)-1-piperazinyl]propyl]-5-ethyl-2,4-dihydro-4-(4-phenylbutyl)-3H-1,2,4-triazol-3-one.

13. The compound of claim 1 which is 2-[3-[4-(3-chlorophenyl)-1-piperazinyl]propyl]-2,4-dihydro-4-(2-phenoxyethyl)-3H-1,2,4-triazol-3-one.

14. The compound of claim 1 which is 2-[3-[4-(3-chlorophenyl)-1-piperazinyl]propyl]-2,4-dihydro-4-[2-(3-chlorophenoxy)ethyl]-3H-1,2,4-triazol-3-one.

15. The compound of claim 1 which is 4-[3-(3-chlorophenoxy)propyl]-2-[3-[4-(3-chlorophenyl)-1-piperazinyl]propyl]-2,4-dihydro-3H-1,2,4-triazol-3-one.

16. The compound of claim 1 which is 2-[3-[4-(3-chlorophenyl)-1-piperazinyl]propyl]-2,4-dihydro-4-[3-[3-(trifluoromethyl)phenoxy]propyl]-3H-1,2,4-triazol-3-one.

17. The compound of claim 1 which is 2-[3-[4-(1,2-benzisothiazol-3-yl)-1-piperazinyl]propyl]-5-ethyl-2,4-dihydro-4-(2-phenoxyethyl)-3H-1,2,4-triazol-3-one.

18. The compound of claim 1 which is 2-[4-[3-[3-ethyl-4,5-dihydro-5-oxo-4-(2-phenoxyethyl)-1H-triazol-1-yl]propyl]-1-piperazinyl]-3-pyridinecarbonitrile.

19. The compound of claim 1 which is 5-ethyl-2,4-dihydro-4-(2-phenoxyethyl)-2-[3-[4-(phenylmethyl)-1-piperazinyl]propyl]-3H-1,2,4-triazol-3-one.

20. The compound of claim 1 which is 5-ethyl-2,4-dihydro-4-(2-phenoxyethyl)-2-[3-[4-(quinolin-2-yl)-1-piperazinyl]propyl]-3H-1,2,4-triazol-3-one.

21. The compound of claim 1 which is 2-[3-[4-(3-chloro-4-fluorophenyl)-1-piperazinyl]propyl]-5-ethyl-2,4-dihydro-4-(2-phenoxyethyl)-3H-1,2,4-triazol-3-one.

22. The compound of claim 1 which is 5-ethyl-2,4-dihydro-4-(2-phenoxyethyl)-2-[3-[4-[3-(trifluoromethyl)phenyl]-1-piperazinyl]propyl]-3H-1,2,4-triazol-3-one.

23. The compound of claim 1 which is 2-[3-[4-(2-chloro-6-pyrazinyl)-1-piperazinyl]propyl]-5-ethyl-2,4-dihydro-4-(2-phenoxyethyl)-3H-1,2,4-triazol-1-one.

24. The compound of claim 1 which is 2-[3-[4-(6-chloro-2-pyridinyl)-1-piperazinyl]propyl]-5-ethyl-2,4-dihydro-4-(2-phenoxyethyl)-3H-1,2,4-triazol-3-one.

25. The method for treating a mammal afflicted with depression comprising administering to said mammal a therapeutically effective antidepressant amount of a compound of claim 1 or a pharmaceutically acceptable acid addition salt thereof.

26. The pharmaceutical composition comprising an antidepressant amount of a compound of claim 1 or a pharmaceutically acceptable acid addition salt thereof and a pharmaceutically acceptable carrier.

27. 5-[3-[4-(3-Chlorophenyl)-1-piperazinyl]propyl]-4-ethyl-2,4-dihydro-2-(2-phenoxyethyl)-3H-1,2,4-triazol-3-one.

28. 5-[3-[4-(3-Chlorophenyl)-1-piperazinyl]propyl]-2,4-dihydro-4-(2-phenoxyethyl)-3H-1,2,4-triazol-3-one.

29. 5-[3-[4-(3-Chlorophenyl)-1-piperazinyl]propyl]-2-ethyl-2,4-dihydro-4-(2-phenoxyethyl)-3H-1,2,4-triazol-3-one.

* * * * *